US012746325B2

(12) United States Patent
Walter et al.

(10) Patent No.: US 12,746,325 B2
(45) Date of Patent: Sep. 29, 2026

(54) DEVICES, SYSTEMS, AND METHODS FOR PRIMING A FLUID MANAGEMENT SYSTEM

(71) Applicant: BOSTON SCIENTIFIC SCIMED, INC., Maple Grove, MN (US)

(72) Inventors: Teagan Jo Walter, Boston, MA (US); Damien Fitzgerald, Tipperary (IE); Randall Maas, Chaska, MN (US); Guilherme Militz, Tipperary (IE); Lakshmi Natarajan, Tipperary (IE); Paul Byrne, Kilkenny (IE); Cassandra Anne Hailson, Marlborough, MA (US); John O'Donnell, Tipperary (IE); Linda Maher, Boston, MA (US); Anant Vaidyanathan Subramaniam, Boston, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 19/193,088

(22) Filed: Apr. 29, 2025

(65) Prior Publication Data

US 2025/0334121 A1 Oct. 30, 2025

Related U.S. Application Data

(60) Provisional application No. 63/640,493, filed on Apr. 30, 2024.

(51) Int. Cl.
*A61M 3/02* (2006.01)
*A61B 1/015* (2006.01)
(Continued)

(52) U.S. Cl.
CPC ........... *A61M 3/0201* (2021.05); *A61B 1/015* (2013.01); *A61M 1/72* (2021.05); *A61M 3/0202* (2021.05);
(Continued)

(58) Field of Classification Search
CPC ...... A61M 2205/12; A61M 2205/3331; A61M 3/0201; A61M 3/0258; A61M 1/72;
(Continued)

(56) References Cited

U.S. PATENT DOCUMENTS

| | | | |
|---|---|---|---|
| 2,474,512 | A | 6/1949 | Bechtold et al. |
| 3,836,287 | A | 9/1974 | Grosholz et al. |

(Continued)

FOREIGN PATENT DOCUMENTS

| | | | |
|---|---|---|---|
| EP | 1898094 | B1 | 3/2009 |
| EP | 2098729 | B1 | 5/2012 |

(Continued)

OTHER PUBLICATIONS

International Search Report and Written Opinion for International Application No. PCT/US2025/026795, dated Aug. 22, 2025. (12 Pages).

*Primary Examiner* — Peter J Bertheaud
(74) *Attorney, Agent, or Firm* — Seager, Tufte & Wickhem, LLP

(57) ABSTRACT

A fluid management system including a fluid management console and a fluid cassette configured to be received within the fluid management console. The console may comprise a housing, a controller housed within the housing, an inflow pump disposed within the housing, and a user input interface. The fluid cassette may comprise a housing defining a fluid pathway therethrough, an inflow tubing extending from the housing, and an outflow tubing extending from the housing. The controller of the fluid management console may be configured to perform a first stage of a priming procedure in response to a user input at the user input interface and a second stage of the priming procedure in response to a pressure drop within the fluid pathway of the fluid cassette.

19 Claims, 10 Drawing Sheets

(51) Int. Cl.
*A61M 1/00* (2006.01)
*F04B 43/00* (2006.01)
*F04B 43/12* (2006.01)
*F04B 51/00* (2006.01)

(52) U.S. Cl.
CPC .......... *F04B 43/0072* (2013.01); *F04B 43/12* (2013.01); *F04B 43/1238* (2013.01); *F04B 43/1253* (2013.01); *F04B 43/1269* (2013.01); *F04B 51/00* (2013.01); *A61M 2205/12* (2013.01); *A61M 2205/3331* (2013.01); *A61M 2205/3334* (2013.01)

(58) Field of Classification Search
CPC ........ A61M 2205/3334; A61M 3/0202; A61B 1/015; F04B 43/12; F04B 43/0072; F04B 43/1269; F04B 43/1238; F04B 51/00; F04B 43/1253
See application file for complete search history.

(56) References Cited

U.S. PATENT DOCUMENTS 4,025,376 A 5/1977 Schirmer
4,179,249 A 12/1979 Guttmann
4,256,442 A 3/1981 Lamadrid et al.
4,363,609 A 12/1982 Cosentino et al.
4,392,791 A 7/1983 Mandroian
4,444,198 A 4/1984 Petre
4,526,574 A 7/1985 Pekkarinen
4,558,996 A 12/1985 Becker
4,650,462 A 3/1987 Desatnick et al.
4,655,197 A 4/1987 Atkinson
4,741,678 A 5/1988 Nehring
4,798,580 A 1/1989 Demeo et al.
4,826,482 A 5/1989 Kamen
4,834,630 A 5/1989 Godwin
4,902,276 A 2/1990 Zakko
4,921,477 A 5/1990 Davis
4,925,376 A 5/1990 Kahler
4,935,005 A 6/1990 Haines
4,994,026 A 2/1991 Fecondini
4,997,347 A 3/1991 Roos
4,998,914 A 3/1991 Wiest et al.
5,005,876 A 4/1991 Fahl
5,041,096 A 8/1991 Beuchat et al.
5,152,746 A 10/1992 Atkinson et al.
5,180,896 A 1/1993 Gibby et al.
5,257,917 A 11/1993 Minarik et al.
5,319,170 A 6/1994 Cassidy
5,380,280 A 1/1995 Peterson
5,381,510 A 1/1995 Ford et al.
5,388,972 A 2/1995 Calhoun et al.
5,403,277 A 4/1995 Dodge et al.
5,437,629 A 8/1995 Goldrath
5,460,490 A 10/1995 Carr et al.
5,464,391 A 11/1995 Devale
5,492,537 A 2/1996 Vancaillie
5,520,638 A 5/1996 O'Quinn et al.
5,522,805 A 6/1996 Vancaillie et al.
5,571,389 A 11/1996 Kerampran
5,586,973 A 12/1996 Lemaire et al.
5,588,815 A 12/1996 Zaleski, II
5,630,798 A 5/1997 Beiser et al.
5,630,799 A 5/1997 Beiser et al.
5,643,203 A 7/1997 Beiser et al.
5,643,302 A 7/1997 Beiser et al.
5,662,611 A 9/1997 Beiser et al.
5,685,821 A 11/1997 Pike
5,709,539 A 1/1998 Hammer et al.
5,729,653 A 3/1998 Magliochetti et al.
5,733,263 A 3/1998 Wheatman
5,800,353 A 9/1998 Mclaurin, Jr.
5,810,770 A 9/1998 Chin et al.
5,830,180 A 11/1998 Chandler et al.
5,840,060 A 11/1998 Beiser et al.
5,868,168 A 2/1999 Mott et al.
5,871,478 A 2/1999 Berrigan
5,875,282 A 2/1999 Jordan et al.
5,882,339 A 3/1999 Beiser et al.
5,919,218 A 7/1999 Carr
5,928,177 A 7/1999 Brugger et al.
5,960,160 A 9/1999 Clark et al.
5,990,465 A 11/1999 Nakaoka et al.
6,024,720 A 2/2000 Chandler et al.
6,046,442 A 4/2000 Kawamura et al.
6,059,544 A 5/2000 Jung et al.
6,077,246 A 6/2000 Kullas et al.
6,142,974 A 11/2000 Kistner et al.
6,146,359 A 11/2000 Carr et al.
6,149,621 A 11/2000 Makihara
6,159,160 A 12/2000 Hsei et al.
6,175,688 B1 1/2001 Cassidy et al.
6,186,752 B1 2/2001 Deniega et al.
6,236,809 B1 5/2001 Cassidy et al.
6,238,366 B1 5/2001 Savage et al.
6,257,265 B1 7/2001 Brunner et al.
6,259,074 B1 7/2001 Brunner et al.
6,261,261 B1 7/2001 Gordon
6,261,283 B1 7/2001 Morgan et al.
6,283,937 B1 9/2001 Takamatsu et al.
6,293,926 B1 9/2001 Sorensen et al.
6,302,864 B1 10/2001 Nowosielski
6,319,221 B1 11/2001 Savage et al.
6,396,583 B1 5/2002 Clare
6,480,257 B2 11/2002 Cassidy et al.
6,494,692 B1 12/2002 Green
6,494,693 B1 12/2002 Sunden
6,512,212 B1 1/2003 Leverne
6,551,080 B2 4/2003 Andersen et al.
6,554,791 B1 4/2003 Cartledge et al.
6,595,957 B1 7/2003 Griffiths et al.
6,626,827 B1 9/2003 Felix et al.
6,632,214 B2 10/2003 Morgan et al.
6,699,184 B2 3/2004 Felix et al.
6,709,417 B1 3/2004 Houle et al.
6,740,074 B2 5/2004 Morgan et al.
6,746,439 B2 6/2004 Lenker
6,775,473 B2 8/2004 Augustine et al.
6,824,528 B1 11/2004 Faries et al.
6,843,099 B2 1/2005 Derek et al.
6,875,194 B2 4/2005 Mackool
6,896,664 B2 5/2005 Novak
6,901,216 B2 5/2005 Jusiak et al.
6,908,451 B2 6/2005 Brody et al.
6,939,111 B2 9/2005 Huitt et al.
6,997,942 B2 2/2006 Machold et al.
7,153,285 B2 12/2006 Lauman et al.
7,195,608 B2 3/2007 Burnett
7,204,821 B1 4/2007 Clare et al.
7,207,966 B2 4/2007 Savare et al.
7,478,999 B2 1/2009 Limoges
7,510,542 B2 3/2009 Blight
7,604,610 B2 10/2009 Shener et al.
7,610,936 B2 11/2009 Spohn et al.
7,645,127 B2 1/2010 Hagen et al.
7,678,070 B2 3/2010 Kumar et al.
7,731,689 B2 6/2010 Prisco et al.
7,798,017 B2 9/2010 Betz
7,819,835 B2 10/2010 Landy et al.
7,880,624 B2 2/2011 Delcastillo et al.
7,896,834 B2 3/2011 Smisson, III et al.
7,918,822 B2 4/2011 Kumar et al.
7,975,491 B2 7/2011 Smisson, III et al.
7,980,835 B2 7/2011 Labanco et al.
7,981,073 B2 7/2011 Mollstam et al.
8,052,399 B2 11/2011 Stemple et al.
8,071,914 B2 12/2011 Azuma
8,087,909 B2 1/2012 Shener
8,100,022 B2 1/2012 Choisnet
8,109,906 B2 2/2012 Smisson, III et al.
8,142,718 B2 3/2012 Tak et al.
8,147,448 B2 4/2012 Sundar et al.
8,167,592 B2 5/2012 Shener-Irmakoglu

(56) References Cited

U.S. PATENT DOCUMENTS 8,178,040 B2 5/2012 Brauer
8,182,241 B2 5/2012 Fulmer
8,187,466 B2 5/2012 Folden et al.
8,206,345 B2 6/2012 Abboud et al.
8,215,931 B2 7/2012 McDowell et al.
8,225,643 B2 7/2012 Abboud et al.
8,226,549 B2 7/2012 Kumar et al.
8,262,603 B2 9/2012 Shener et al.
8,264,363 B2 9/2012 DelCastillo et al.
8,297,955 B2 10/2012 Fuji
8,308,726 B2 11/2012 Kumar et al.
8,360,737 B2 1/2013 Smisson, III et al.
8,366,667 B2 2/2013 Chan et al.
8,377,000 B2 2/2013 Pfouts
8,382,447 B2 2/2013 Wang et al.
8,388,570 B2 3/2013 Kumar et al.
8,444,592 B2 5/2013 Williams et al.
8,449,500 B2 5/2013 DelCastillo et al.
8,512,283 B2 8/2013 Kumar et al.
8,562,577 B2 10/2013 Michaels et al.
8,568,424 B2 10/2013 Shugrue et al.
8,591,464 B2 11/2013 Kumar et al.
8,597,228 B2 12/2013 Pyles et al.
8,620,149 B2 12/2013 Entenman et al.
8,630,737 B2 1/2014 Oda
8,652,089 B2 2/2014 Kumar et al.
8,764,408 B2 7/2014 Smisson, III et al.
8,790,096 B2 7/2014 Sorenson
8,790,303 B2 7/2014 Williams et al.
8,803,044 B2 8/2014 Kienman et al.
8,870,866 B2 10/2014 Woloszko
8,876,489 B2 11/2014 Shener
8,911,363 B2 12/2014 Kumar et al.
8,920,372 B2 12/2014 Faries, Jr. et al.
8,934,764 B2 1/2015 Wei et al.
9,027,389 B2 5/2015 Abboud et al.
9,028,398 B2 5/2015 Kumar et al.
9,072,540 B2 7/2015 Jarnagin et al.
9,101,701 B2 8/2015 Kumar et al.
9,155,453 B2 10/2015 Kumar et al.
9,173,987 B2 11/2015 Meyer et al.
9,211,381 B2 12/2015 Faries et al.
9,239,049 B2 1/2016 Jarnagin et al.
9,254,164 B2 2/2016 Wolosko
9,272,086 B2 3/2016 Williams et al.
9,289,110 B2 3/2016 Woolford et al.
9,322,729 B2 4/2016 Heide et al.
9,474,848 B2 10/2016 Williams et al.
9,482,216 B2 11/2016 Sorenson
9,492,071 B2 11/2016 Woolford et al.
9,498,586 B2 11/2016 Smisson, III et al.
9,511,184 B2 12/2016 Wookford et al.
9,526,829 B2 12/2016 Spohn et al.
9,603,990 B2 3/2017 Woolford
9,737,672 B2 8/2017 Landy et al.
9,764,100 B2 9/2017 Faries, Jr. et al.
9,770,541 B2 9/2017 Carr et al.
9,889,246 B2 2/2018 Woolford
9,962,472 B2 5/2018 Woolford et al.
10,028,763 B2 7/2018 Kumar et al.
10,077,767 B2 9/2018 Macari et al.
10,137,257 B2 11/2018 Landy, III et al.
10,518,005 B2 12/2019 Carr et al.
12,318,527 B2 * 6/2025 Maher ................. A61M 60/554
2003/0004470 A1 1/2003 Hickerson et al.
2003/0216689 A1 11/2003 Bouhuijs et al.
2004/0037724 A1 2/2004 Haser et al.
2004/0170409 A1 9/2004 Faries, Jr. et al.
2005/0069436 A1 3/2005 Shibasaki et al.
2005/0163637 A1 7/2005 Chang et al.
2005/0203469 A1 9/2005 Bobroff et al.
2005/0254978 A1 11/2005 Huber et al.
2006/0122556 A1 6/2006 Kumar et al.
2006/0185464 A1 8/2006 Telep et al.
2007/0078370 A1 4/2007 Shener et al.
2007/0265689 A1 11/2007 Frey
2008/0015515 A1 1/2008 Hopkins et al.
2008/0091071 A1 4/2008 Kumar et al.
2008/0154095 A1 6/2008 Stubkjaer et al.
2009/0129944 A1 5/2009 Stemple et al.
2010/0036313 A1 2/2010 Shener et al.
2010/0228222 A1 9/2010 Williams et al.
2012/0289894 A1 11/2012 Douglas et al.
2013/0079596 A1 3/2013 Smith
2013/0267892 A1 10/2013 Woolford
2015/0190274 A1 7/2015 Landy et al.
2016/0123320 A1 5/2016 Tsoukalis
2016/0166758 A1 6/2016 Norman et al.
2017/0000957 A1 1/2017 Carr et al.
2017/0184088 A1 6/2017 Macari et al.
2017/0203028 A1 7/2017 Carr et al.
2017/0281865 A1 10/2017 Wells et al.
2018/0147368 A1 5/2018 Landy, III et al.
2018/0147369 A1 5/2018 Landy, III et al.
2018/0333295 A1 11/2018 Landy et al.
2018/0361055 A1 12/2018 Pereira et al.
2019/0120223 A1 4/2019 Macari et al.
2019/0366017 A1 12/2019 Minahan
2020/0200313 A1 6/2020 Chu et al.
2020/0297900 A1 9/2020 Holigan et al.
2020/0405955 A1 12/2020 Shah et al.
2021/0128815 A1 5/2021 Byrne et al.
2021/0236728 A1 8/2021 Fanning et al.
2021/0268182 A1 9/2021 O'Donnell et al.
2022/0031392 A1 2/2022 Maher et al.
2022/0143299 A1 5/2022 Sutter et al.
2022/0370706 A1 11/2022 Meganck et al.
2022/0400936 A1 12/2022 Velazquez et al.
2023/0042236 A1 2/2023 Chu
2023/0055028 A1 * 2/2023 Maher .................. A61M 60/113
2023/0398286 A1 12/2023 Jacobson et al.
2025/0151992 A1 5/2025 Maher et al.
2025/0153161 A1 5/2025 Maher et al.

FOREIGN PATENT DOCUMENTS

EP 2427231 B1 11/2014
WO 8700759 A1 2/1987
WO 9217040 A1 10/1992
WO 9322979 A1 11/1993
WO 9640331 A1 12/1996
WO 9716220 A1 5/1997
WO 9746271 A1 12/1997
WO 2018236513 A1 12/2018

* cited by examiner

DEVICES, SYSTEMS, AND METHODS FOR PRIMING A FLUID MANAGEMENT SYSTEM

CROSS-REFERENCE TO RELATED APPLICATIONS

The application claims the benefit of U.S. Provisional Patent Application Ser. No. 63/640,493, filed on Apr. 30, 2024, the disclosure of which is incorporated herein by reference.

TECHNICAL FIELD

The disclosure is directed to a fluid management system. More particularly, the disclosure is directed to priming a fluid management system.

BACKGROUND

Flexible ureteroscopy (fURS), gynecology, and other endoscopic procedures require the circulation of fluid for several reasons. Fluid management systems may be used to deliver fluid to an anatomical cite from a reservoir at a desired pressure and/or flowrate via a peristaltic or roller pump. Fluid management systems may adjust the flowrate and/or pressure at which fluid is delivered from the reservoir based on data collected from a procedural device, such as, but not limited to, pressure readings sensed and/or obtained by the fluid management system. The fluid management system may utilize a disposable fluid tubing set installed with a pump console to provide the fluid to the patient. There is an ongoing need to provide alternative configurations of the components of fluid management systems, to facilitate the use thereof.

BRIEF SUMMARY

This disclosure provides design, material, manufacturing method, and use alternatives for components of a fluid management system. In a first example, a fluid management system may comprise a fluid management console and a fluid cassette configured to be received within a receptacle of the housing of the fluid management console. The fluid management console may comprise a housing, a controller housed within the housing, an inflow pump disposed within the housing, and a user input interface. The fluid cassette may comprise a housing defining a fluid pathway therethrough, an inflow tubing extending from the housing, and an outflow tubing extending from the housing. The controller of the fluid management console may be configured to perform a first stage of a priming procedure in response to a user input at the user input interface and a second stage of the priming procedure in response to a pressure drop within the fluid pathway of the fluid cassette.

Alternatively or additionally to any of the examples above, in another example, the fluid management system may further comprise a clamp secured to the outflow tubing. The clamp may be movable between a closed configuration configured to block a flow of fluid through the outflow tubing and an open configuration configured to allow a flow of fluid through the outflow tubing.

Alternatively or additionally to any of the examples above, in another example, the clamp may be in the closed configuration during the first stage of the priming procedure and the open configuration during the second stage of the priming procedure.

Alternatively or additionally to any of the examples above, in another example, the fluid management system may further comprise one or more pressure sensors disposed within fluid management console. The one or more pressure sensors may be configured to monitor a pressure within the fluid pathway of the fluid cassette.

Alternatively or additionally to any of the examples above, in another example, during the first stage of the priming procedure, the controller may be configured to activate the inflow pump.

Alternatively or additionally to any of the examples above, in another example, if the second stage of the priming procedure is not initiated within a predetermined length of time after completion of the first stage of the priming procedure, the controller may be configured to instruct the user to repeat the first stage of the priming procedure.

Alternatively or additionally to any of the examples above, in another example, the predetermined length of time may be one hour.

Alternatively or additionally to any of the examples above, in another example, during the first stage of the priming procedure, the controller may be configured to monitor a pressure within the fluid pathway of the fluid cassette.

Alternatively or additionally to any of the examples above, in another example, if the pressure within the fluid pathway exceeds a predetermined maximum pressure, the controller may be configured to issue a high-pressure error.

Alternatively or additionally to any of the examples above, in another example, if the pressure the fluid pathway drops, the controller may be configured to issue a pressure drop error.

Alternatively or additionally to any of the examples above, in another example, if a cycle time of the first stage of the priming procedure exceeds a predetermined maximum cycle time, the controller may be configured to issue a timeout error.

Alternatively or additionally to any of the examples above, in another example, the controller may be configured to increase a revolutions per minute of the inflow pump until a predetermined maximum speed is achieved.

Alternatively or additionally to any of the examples above, in another example, upon reaching a predetermined stop pressure and a minimum runtime, the first stage of the priming procedure may be successfully completed.

Alternatively or additionally to any of the examples above, in another example, during the second stage of the priming procedure a revolutions per minute of the inflow pump may be increased until a threshold pressure within the fluid pathway of the fluid cassette is reached.

Alternatively or additionally to any of the examples above, in another example, the second stage of the priming procedure may be successfully completed with a minimum fluid volume has been delivered through the fluid pathway of the fluid cassette or a minimum cycle time has elapsed.

In another example, a fluid management system may comprise a fluid management console and a fluid cassette configured to be received within a receptacle of the housing of the fluid management console. The fluid management console may comprise a housing, a controller housed within the housing, an inflow pump disposed within the housing, one or more pressure sensors disposed, and a user input interface. The fluid cassette may comprise a housing defining a fluid pathway therethrough, an inflow tubing extending from the housing, an outflow tubing extending from the housing, and a clamp secured to the outflow tubing. The clamp may be movable between a closed configuration configured to block a flow of fluid through the outflow tubing and an open configuration configured to allow a flow of fluid through the outflow tubing. The controller of the fluid management console may be configured to perform a first stage of a priming procedure in response to a user input at the user input interface and a second stage of the priming procedure in response to a pressure drop within the fluid pathway of the fluid cassette.

Alternatively or additionally to any of the examples above, in another example, opening the clamp may initiate the second stage of the priming procedure.

Alternatively or additionally to any of the examples above, in another example, the first stage of the priming procedure may be configured to remove air from the inflow tubing, the fluid pathway of the fluid cassette, and the outflow tubing to a location of the clamp.

Alternatively or additionally to any of the examples above, in another example, the second stage of the priming procedure may be configured to remove air from an entirety of the outflow tubing and a connected device.

In another example, a fluid management system may comprise a fluid management console and a fluid cassette configured to be received within a receptacle of the housing of the fluid management console. The fluid management console may comprise a housing, a controller housed within the housing, an inflow pump disposed within the housing, and a user input interface. The fluid cassette may comprise a housing defining a fluid pathway therethrough, an inflow tubing extending from the housing, and an outflow tubing extending from the housing. The controller of the fluid management console may be configured to perform a first stage of a priming procedure in response to a user input at the user input interface and a second stage of the priming procedure in response to a pressure drop within the fluid pathway of the fluid cassette, the second stage of the priming procedure configured to begin after a successful completion of the first stage of the priming procedure.

The above summary of some embodiments is not intended to describe each disclosed embodiment or every implementation of the present disclosure. The Figures, and Detailed Description, which follow, more particularly exemplify some of these embodiments

BRIEF DESCRIPTION OF THE DRAWINGS

The disclosure may be more completely understood in consideration of the following detailed description in connection with the accompanying drawings, in which.

Figure 1:
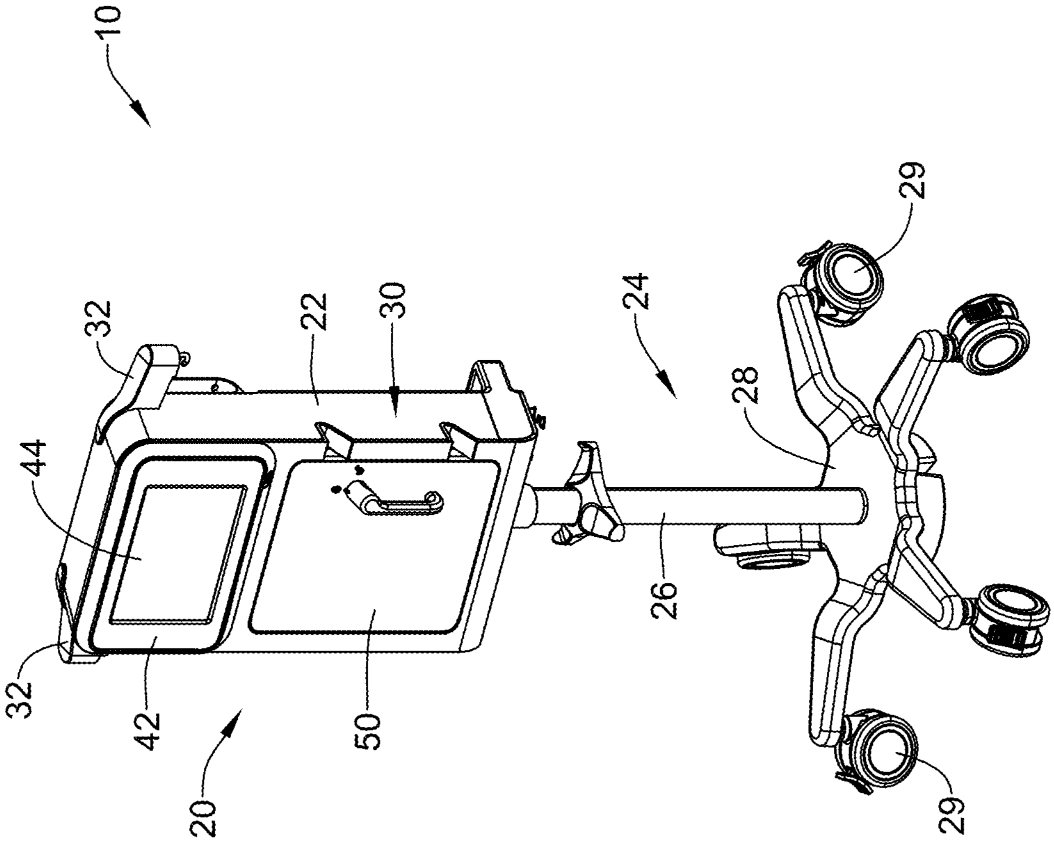
FIG. 1 is a perspective view of an exemplary console of a fluid management system.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar structures in different drawings are numbered the same. The drawings, which are not necessarily to scale, depict illustrative embodiments and are not intended to limit the scope of the disclosure.

Some fluid management systems for use in flexible ureteroscopy (fURS) procedures (e.g., ureteroscopy, percutaneous nephrolithotomy (PCNL), benign prostatic hyperplasia (BPH), transurethral resection of the prostate (TURP), etc.), gynecology, and other endoscopic procedures may control the flow of fluid into the body cavity and/or regulate body cavity pressure and/or the flowrate of fluid flow to the body cavity using an inflow and/or outflow pump of the fluid management system. The inflow pump may deliver fluid through inflow tubing of a fluid tubing set to the patient and/or the outflow pump may remove fluid through outflow tubing of a fluid tubing set from the patient. The fluid management system may include one or more sensors providing signals to the controller of the fluid management system to control the fluid flow.

In some instances, in which the fluid management system is used in conjunction with an endoscope device such as, but not limited to, a LithoVue™ Elite endoscope, the fluid management system may control the fluid flow using pressure and/or temperature data from the endoscope or other endoscopic device. Direct regulation of the intracavity pressure during a medical procedure using a pressure sensor on the endoscope may allow the fluid management system to safely control the fluid pressure with the body cavity.

FIG. 1 is a schematic view of a fluid management system 10 that may be used in an endoscopic procedure, such as fURS procedures. The fluid management system 10 may be coupled to a medical device (not shown), such as an endoscope, that allows flow of fluid therethrough. As noted above, in some instances the endoscope may include a pressure sensor, such as the LithoVue™ Elite endoscope, or other endoscope. In some instances, the endoscope may include a temperature sensor to provide intracavity temperature feedback to the fluid management system 10, a pressure sensor to provide intracavity pressure feedback to the fluid management system 10, and/or a camera to provide visual feedback to the fluid management system 10.

The fluid management system 10 also includes a fluid management unit or console 20 including a controller 30 housed within a housing 22 of the console 20. In some instances, the console 20 may be portable and/or mobile such that the console 20 may be moved as desired. For instance, the console 20 may be mounted on a wheeled cart 24. For example, the wheeled cart 24 may include a pole 26 extending upward from a base 28. The base 28 may include a plurality of wheels 29 (e.g., caster wheels), allowing the cart 24 to be wheeled around to a desired location. In other instances, the console 20 may be provided with another form of cart, configured to be positioned on a flat surface, mounted to a wall, etc.

The fluid management system 10 may also include one or more user input interface components such as a touch screen interface 42. The touch screen interface 42 includes a display screen 44 and may include switches or knobs in addition to touch capabilities. In some embodiments, the controller 30 may include the touch screen interface 42 and/or the display screen 44. The user input interface, e.g., touch screen interface 42, allows the user to input/adjust various functions of the fluid management system 10 such as, for example flowrate, pressure, and/or temperature. The user may also configure parameters and alarms (such as, but not limited to, a max pressure alarm), information to be displayed, and the procedure mode. The user input interface, e.g., touch screen interface 42, allows the user to add, change, and/or discontinue the use of various modular systems within the fluid management system 10. The user input interface, e.g., touch screen interface 42, may also be used to change the fluid management system 10 between automatic and manual modes for various procedures. It is contemplated that other systems configured to receive user input may be used in place of or in addition to the touch screen interface 42 such as, but not limited to, voice commands.

The touch screen interface 42 may be configured to include selectable areas like buttons and/or may provide a functionality similar to physical buttons as would be understood by those skilled in the art. The display screen 44 may be configured to show icons related to modular systems and devices included in the fluid management system 10. The display screen 44 may also include a fluid flowrate and/or fluid pressure display. In some embodiments, operating parameters may be adjusted by touching a corresponding portion of the touch screen interface 42. The touch screen interface 42 may also display visual alerts and/or audio alarms if parameters (e.g., flowrate, temperature, etc.) are above or below predetermined thresholds and/or ranges. In some embodiments, the fluid management system 10 may also include further user interface components such as an optional foot pedal, a fluid warmer user interface, a fluid control interface, or other device to manually control various modular systems. For example, an optional foot pedal may be used to manually control flowrate. Some illustrative display screens 44 and other user interface components are described in commonly assigned U.S. Patent Application Publication No. 2018/0361055, titled AUTOMATED FLUID MANAGEMENT SYSTEM, the entire disclosure of which is hereby incorporated by reference.

The user input interface, e.g., touch screen interface 42, may be operatively connected to or a part of the controller 30. The controller 30 may be a CPU, including a computer, tablet computer, or other processing device. The controller 30 may be operatively connected to one or more system components such as, for example, an inflow pump, a fluid warming system, and a fluid deficit management system. In some embodiments, these features may be integrated into a single unit. The controller 30 is capable of and configured to perform various functions such as calculation, control, computation, display, etc. The controller 30 is also capable of tracking and storing data pertaining to the operations of the fluid management system 10 and each component thereof. In some embodiments, the controller 30 may include wired and/or wireless network communication capabilities, such as ethernet or Wi-Fi, through which the controller 30 may be connected to, for example, a local area network. The controller 30 may also receive signals from one or more of the sensors of the fluid management system 10. In some embodiments, the controller 30 may communicate with databases for best practice suggestions and the maintenance of patient records which may be displayed to the user on the display screen 44.

The fluid flowrate or the fluid pressure of fluid provided by the fluid management system 10 at any given time may be displayed on the display screen 44 to allow the operating room (OR) visibility for any changes. If the OR personnel notice a change in fluid flowrate or fluid pressure that is either too high or too low, the user may manually adjust the fluid flowrate or the fluid pressure back to a preferred level. The fluid management system 10 may also monitor and automatically adjust the fluid flowrate or the fluid pressure based on previously set parameters, as discussed herein.

An illustrative fluid management unit may include one or more fluid container supports, such as fluid supply source hanger(s) 32, each of which may support a fluid supply source (e.g., fluid bag). In some embodiments, placement and/or weight of the fluid supply source(s) hanging from the fluid supply source hanger(s) 32 may be detected using a remote sensor and/or a supply load cell associated with and/or operatively coupled to each fluid supply source hanger 32 and/or fluid container support. The controller 30 may be in electronic communication with the supply load cell. The fluid supply source hanger(s) 32 may be configured to receive a variety of sizes of the first fluid supply source(s) such as, for example, 1 liter (L) to 5 L fluid bags (e.g., saline bags). It will be understood that any number of fluid supply sources may be used. The fluid supply source hanger(s) 32 may extend from the housing 22 of the console 20 and may include one or more hooks from which one or more fluid supply sources may be suspended. In some embodiments, the fluid used in the fluid management unit may be 0.9% saline. However, it will be understood that a variety of other fluids of varying viscosities, concentrations, mixtures, and/or consistencies may be used depending on the procedure.

In some embodiments, the fluid management unit may include one or more collection containers (not shown), for collecting waste fluid during a medical procedure. The collection containers (e.g., canisters) may be in fluid communication with a vacuum pump to provide suction for drawing fluid into the collection containers. The vacuum pump may be operatively and/or electronically connected to the controller 30. In some embodiments, the vacuum pump may be disposed within the fluid management system 10. Other configurations are also contemplated. In some embodiments, the collection container(s) may be operatively coupled to a collection load cell to detect placement and/or weight of fluid in the collection container(s) to contribute to a fluid deficit calculation.

Figure 2:
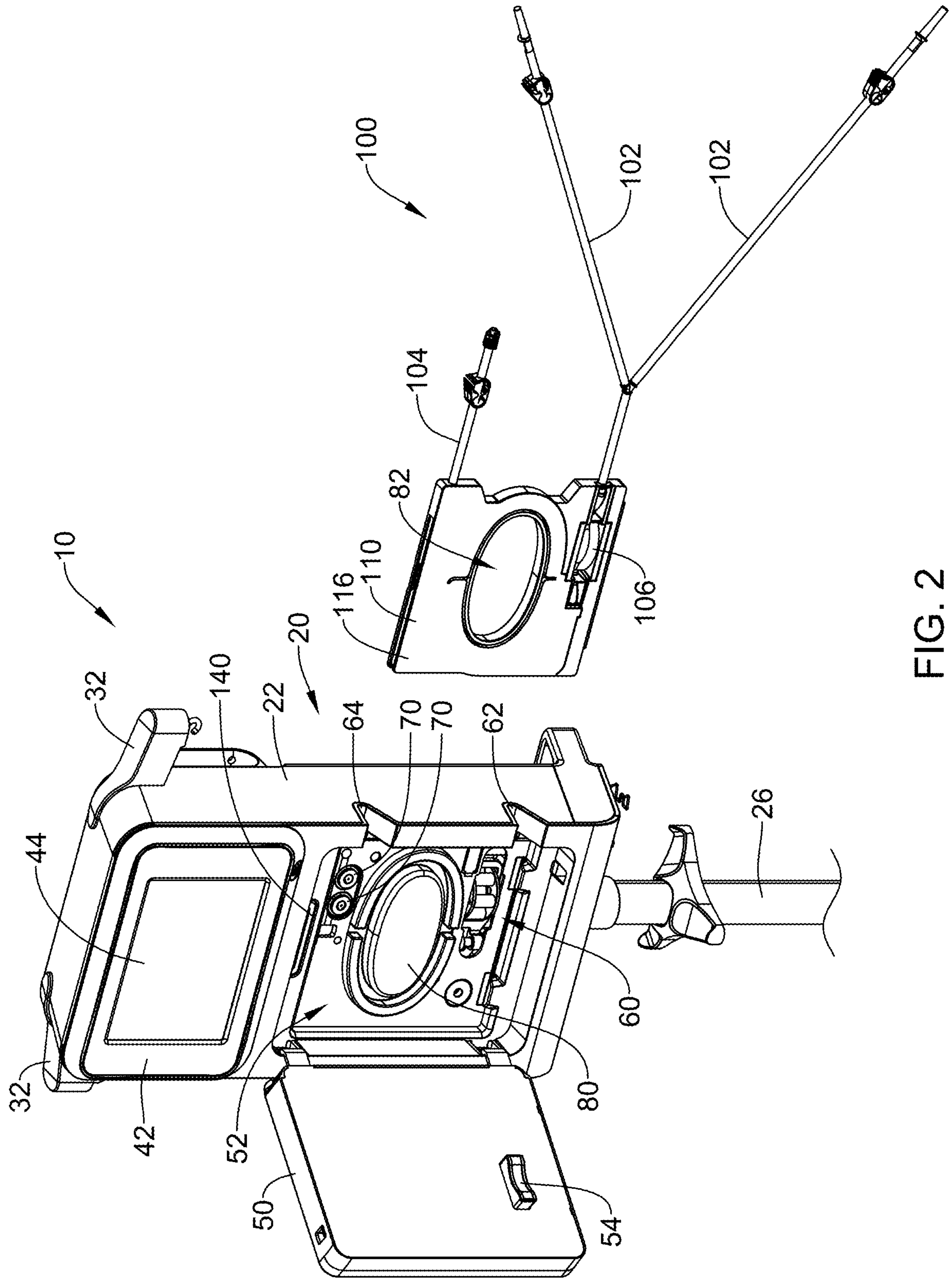
FIG. 2 is a perspective view of a fluid management system including the console of FIG. 1 with a disposable fluid tubing set.

The console 20 may include a door 50 hingedly attached to the housing 22 of the console 20. As shown in FIG. 2, the door 50 may be opened to access a receptacle 52 configured to receive a fluid cassette 110 of a single use fluid tubing set 100 therein. The fluid management system 10 may include an inflow pump 60 configured to operatively engage the fluid tubing set 100 to pump and/or transfer fluid from a fluid supply source (e.g., a fluid bag, etc.) through the fluid tubing set 100 to a treatment site during a medical procedure. For example, the inflow pump 60 may be a roller pump or peristaltic pump positioned in the receptacle 52 configured to engage a length of flexible pump tubing 106 of the fluid cassette 110 when inserted therein. The door 50 may include an occlusion bed 54 mounted on the interior surface of the door 50. The occlusion bed 54 is configured to engage the length of flexible pump tubing 106 of the fluid cassette 110 when the door 50 is closed, to compress the length of flexible pump tubing 106 between the occlusion bed 54 and the inflow pump 60. The occlusion bed 54 may include a concave surface configured to engage the length of flexible pump tubing 106, which extends in an arcuate path around the inflow pump 60.

The inflow pump 60 may be electrically driven and may receive power from a line source such as a wall outlet, an external or internal electrical storage device such as a disposable or rechargeable battery, and/or an internal power supply. The inflow pump 60 may operate at any desired speed sufficient to deliver fluid at a desired pressure such as, for example, 5 mmHg to 50 mmHg, and/or at a target fluid flowrate or a target fluid pressure. As noted herein, the inflow pump 60 may be automatically adjusted based on, for example, pressure and/or temperature readings within the treatment site and/or visual feedback from the medical device attached thereto and inserted into the treatment site. In some embodiments, the controller 30 may be configured to control the inflow pump 60 to maintain a target fluid flowrate or target fluid pressure based on a set of system operating parameters. In some embodiments, the controller 30 may be configured to control the inflow pump 60 to maintain a desired fluid pressure at the treatment site or a desired flowrate based on a set of system operating parameters.

The inflow pump 60 may also be manually adjusted via, for example, an optional foot pedal, the touch screen interface 42, voice commands, or a separate fluid controller. While not explicitly shown, the fluid controller may be a separate user interface including buttons that allow the user to increase or decrease the inflow pump 60. Alternatively, the fluid controller may be incorporated into the controller 30 and receive input via the touch screen interface 42, voice commands, or other means of input. It will be understood that any number of pumps may be used. In some embodiments, the fluid management system 10 may include multiple pumps having different flow capabilities. In some embodiments, a flow meter may be located before and/or after the inflow pump 60.

The fluid management system 10 may be user selectable between different modes based on the procedure, patient characteristics, etc. For example, different modes may include, but are not limited to, fURS Mode, BPH Mode, Hysteroscopy Mode, Cystoscopy Mode, etc. Once a mode has been selected by the user, mode parameters such as fluid flowrate, fluid pressure, fluid deficit, and temperature may be provided to the user via the display screen. The exemplary parameters of the specific modes may be previously determined and loaded onto the controller 30 using, for example, software. Thus, when a user selects a procedure from an initial display on the touch screen interface display screen 44, these known parameters may be loaded from the controller 30 to the various components of the fluid management system 10. The fluid management system 10 may also be user selectable between automatic and manual mode. For example, for certain procedures, the user may wish to manually adjust a fluid flowrate, fluid pressure, and/or other parameters. Once the user has selected the manual mode on, for example, the touch screen interface 42, the user may the adjust fluid flowrate or fluid pressure via other manual interfaces such as an optional foot pedal, voice commands, or the fluid control interface. If the user selects an automatic mode, the user may be prompted to select or input via the touch screen interface 42 which medical device (e.g., endoscope) is being used so that the controller 30 may determine if data obtained from the medical device can be used to facilitate control of the fluid management system 10. In some embodiments, the fluid management system 10 may be configured to verify the medical device (e.g., endoscope) selected is actually being used prior to using the collected data.

The single use tubing set 100 may include inflow tubing 102 providing a fluid inflow from the fluid supply source into the interior of the fluid cassette 110. In some instances, the inflow tubing 102 may include a bifurcated tubing with a first tubing section fluidly connected to a first fluid supply source and a second tubing section fluidly connected to a second fluid supply source. The first and second tubing sections may converge (such as at a Y-fitting) to a common tubing section extending to the fluid cassette 110. The end of the first tubing section and/or the second tubing section may include a bag spike, or other connector for connecting to the fluid supply source(s). The single use tubing set 100 may also include outflow tubing 104 providing a fluid outflow from the interior of the cassette 110 to a medical device connected thereto. The single use tubing set 100, including the fluid cassette 110, the inflow tubing 102, and the outflow tubing 104, may be disposable and provided sterile and ready to use.

When the fluid cassette 110 is installed in the receptacle 52 and the door 50 is closed, the inflow tubing 102 may pass through a channel 62 extending through a wall of the housing 22 of the console 20 to an exterior of the console 20. Likewise, when the fluid cassette 110 is installed in the receptacle 52 and the door 50 is closed, the outflow tubing 104 may pass through a channel 64 extending through a wall of the housing 22 of the console to an exterior of the console 20. The channel 62 and the channel 64 may both extend from the exterior of the console 20 to the receptacle 52. In some instances, both the channel 62 and the channel 64 may be located on the same sidewall of the console 20 such that both the inflow tubing 102 and the outflow tubing 104 extend from the console 20 on the same side of the console 20.

In some embodiments, the fluid management system 10 may include a fluid warming system 80, as shown in more detail in FIG. 2, for heating fluid to be delivered to the patient. The fluid warming system 80 may be an inductive heating system in some instances. In other instances, the fluid warming system 80 may be an infrared fluid warming system. Other fluid warming system configurations and methods may also be used, as desired. For example, the fluid warming system 80 may include one or more heat sources such as, for example a platen system or an inline coil in the fluid supply line to heat the fluid using electrical energy. Fluid warming may be specifically designed and tailored to the flowrates required in the specific application of the fluid management system 10. Some illustrative fluid warming systems are described in commonly assigned U.S. Patent Application Publication No. 2018/0361055, titled AUTOMATED FLUID MANAGEMENT SYSTEM, the entire disclosure of which is hereby incorporated by reference.

The fluid warming system 80 may include a heater configured to interact with the fluid cassette 110 to heat fluid passing therethrough. When the fluid cassette 110 is coupled with the heater, a susceptor positioned in the fluid path of the cassette 110 may be positioned within an induction coil of the fluid warming system 80 and be configured to heat the fluid flowing through or past the susceptor as the fluid passes through the fluid flow path of the cassette 110.

While not explicitly shown, the fluid warming system 80 may include a heater user interface included with or separate from the touch screen interface 42. In one example, the heater user interface may simply be a display screen providing a digital display of the temperature of the fluid entering and/or exiting the susceptor in the fluid flow path of the cassette 110. In another embodiment, the user interface may also include temperature adjustment buttons to increase or decrease the temperature of the fluid exiting the cassette 110. In this embodiment, the heater user interface and/or the display screen may indicate the current temperature of the fluid exiting the cassette 110 as well as the target temperature to be reached. It is noted that all information output from the fluid warming system 80 may be transmitted directly to the display screen 44 such that no heater user interface is necessary.

The fluid warming system 80 may include one or more sensors configured to monitor the fluid flowing therethrough. For example, temperature sensors may be mounted in the fluid warming system 80 such that they detect the temperature of the fluid flowing through the fluid cassette 110. In some embodiments, a first temperature sensor may be located at or near the fluid inlet to the susceptor and/or the fluid outlet from the susceptor so that they detect the temperature of fluid flowing through the fluid cassette 110 prior to the fluid entering the susceptor and after fluid exits the susceptor. In some embodiments, additional sensors may be located at a medial portion of the susceptor so that they detect a progression of temperature increase of the fluid in the fluid cassette 110.

The console 20 may further include one or more additional sensors, such as a pressure sensor and/or a bubble sensor. For instance, the console 20 may include a pressure sensor 70, illustrated as a pair of pressure sensors, configured to monitor a pump pressure (i.e., system pressure) of fluid exiting the cassette 110 and flowing through the outflow tubing 104 to a surgical site. The fluid cassette 110 may include a corresponding pressure sensor interface 72, such as a flexible membrane, (shown in FIG. 4) that allow the pressure sensor 70 to monitor the pressure of fluid flowing through the fluid cassette 110 when the fluid cassette 110 is installed in the receptacle 52 of the console 20. The pressure sensor 70 may send information to the controller 30 and/or display screen 44.

Figure 3:
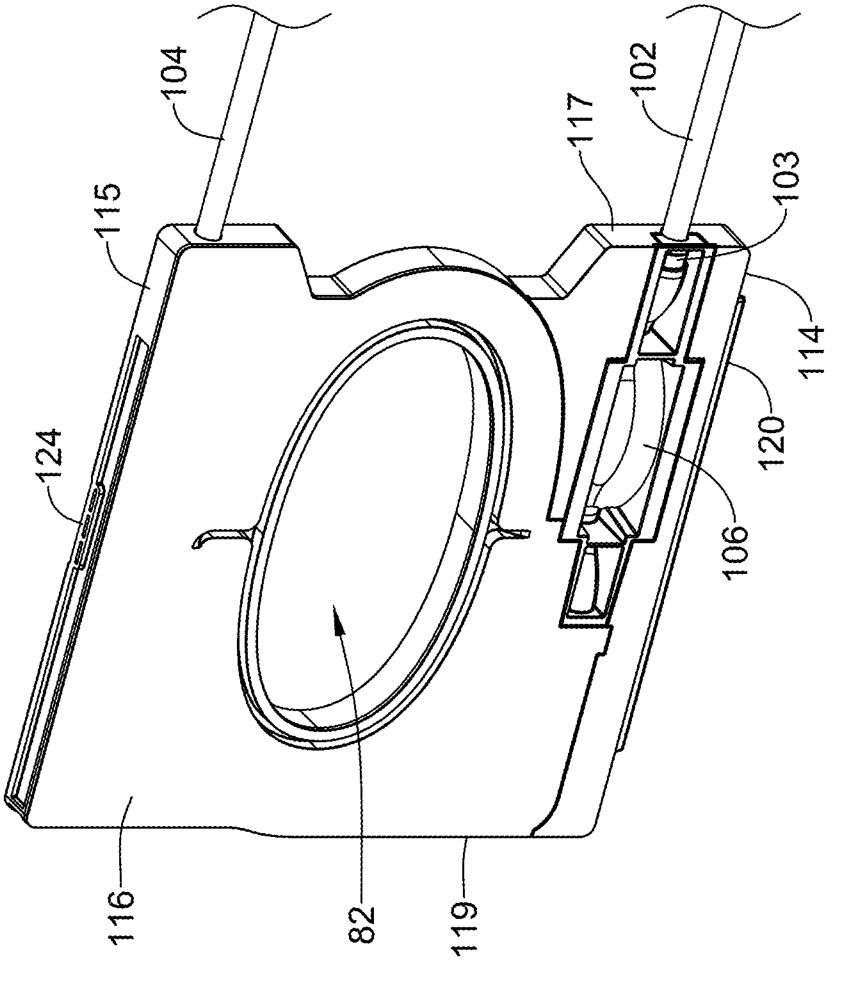
FIG. 3 is a perspective view of the front side of the fluid cassette of the disposable tubing set of FIG. 2.
Figure 4:
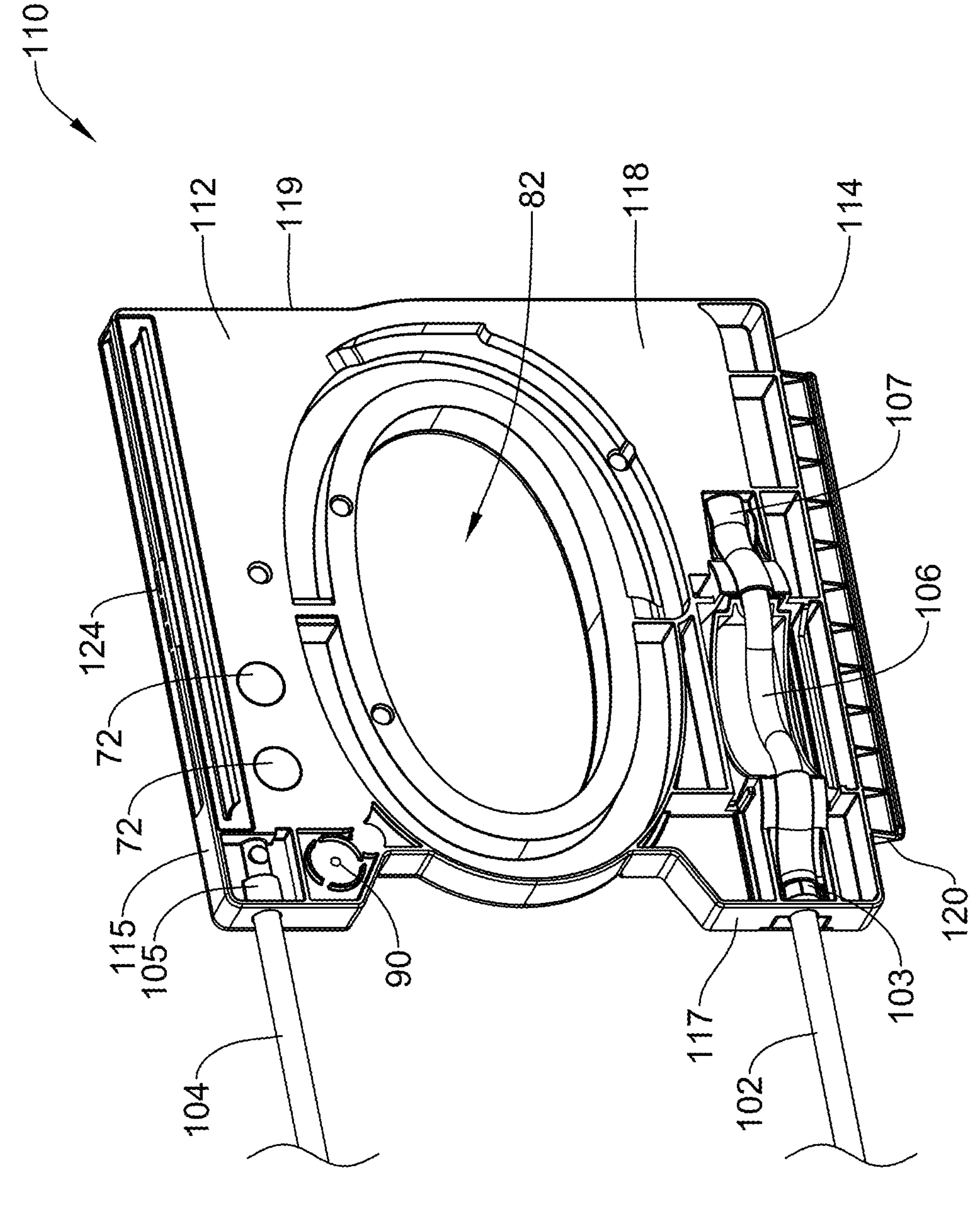
FIG. 4 is perspective view of the rear side of the fluid cassette of the disposable fluid tubing set of FIG. 2.

Additional features of the cassette 110 of the fluid tubing set 100 are illustrated in FIGS. 3 and 4. The fluid cassette 110 may include a housing 112 defining a fluid pathway through an interior of the housing 112. The fluid cassette 110 may include a front face 116 and a rear face 118 opposite the front face 116. The front face 116 is configured to face the door 50 of the console 20 when loaded in the receptacle 52, and the rear face 118 is configured to face a rear wall of the receptacle 52 of the console 20 when loaded in the receptacle 52. The fluid cassette 110 may also include an upper edge 115 and a lower edge 114 opposite the upper edge 115. The fluid cassette 110 may also include a first side edge 117 and a second side edge 119, opposite the first side edge 117. Both, the inflow tubing 102 and the outflow tubing 104 may extend from the first side edge 117. The housing 112 of the fluid cassette 110 may also include an opening 82, such as an oval opening, extending through the housing 112 from the front face 116 to the rear face 118. The opening 82 may extend a majority of the length of the housing 112 (i.e., a majority of the distance between the lateral edges of the housing 112) and/or a majority of the height of the housing 112 (i.e., a majority of the distance between the upper edge and the lower edge of the housing 112), in some instances. The opening 82 may be configured to receive an elevated portion of the rear wall of the receptacle 52, shown in FIG. 1 as the fluid warming system 80. The elevated portion of the rear wall of the receptacle 52 may be an oval shape sized to fit through the oval shaped opening 82 of the housing 112 of the fluid cassette 110 when the fluid cassette 110 is in its loaded position in the receptacle 52. In embodiments, in which the console 20 lacks a fluid warming system, the elevated portion of the rear wall of the receptacle 52 may still be present. Insertion of the elevated portion of the rear wall of the receptacle 52 through the opening 82 of the fluid cassette 110 may facilitate proper alignment of the fluid cassette 110 in the receptacle 52, for example.

In some embodiments, the fluid cassette 110 may include a fluid inlet port 103 and a fluid outlet port 105 located at a lateral side of the fluid cassette 110 accessible from the first side edge 117 of the fluid cassette 110. The fluid inlet port 103 may be coupled to the inflow tubing 102 and the fluid outlet port 105 may be coupled to the outflow tubing 104, with the inflow tubing 102 and the outflow tubing 104 extending laterally from the first side edge 117. The fluid inlet port 103 may be located below (e.g., closer to the lower edge 114) than the fluid outlet port 105. Thus, the inflow tubing 102 may extend laterally from the first side edge 117 at a location below (e.g., closer to the lower edge 114) than the location that the outflow tubing 104 extends from the first side edge 117. The cassette 110 may define an internal fluid pathway through an interior of the cassette housing 112 of the cassette 110 between the fluid inlet port 103 and the fluid outlet port 105. In embodiments of the fluid management system 10 including fluid warming capabilities, the internal fluid pathway may include the susceptor. The length of flexible pump tubing 106 of the cassette 110, configured to engage and be compressed by the rollers of the inflow pump 60, may extend from the fluid inlet port 103 to a connection 107 of the cassette 110 leading to the fluid pathway defined through the interior of the cassette 110. The flexible pump tubing 106 may be a discrete length of tubing separate from the inflow tubing 102 and the outflow tubing 104. In some instances, the flexible pump tubing 106 may extend through an arcuate pathway between the fluid inlet port 103 to the connection 107, such that the flexible pump tubing 106 follows the rotational path of the rollers of the inflow pump 60. The inlet port 103, the outlet port 105, and/or the connection 107 may be formed as a portion of the cassette housing 112 or may be formed separately and connected thereto.

The fluid cassette 110 may also include an air vent valve 90 configured to release air from the interior of the fluid cassette 110 to atmosphere. For example, the fluid cassette 110 may include an air vent including a hydrophobic membrane, allowing air, including bubbles entrained in the fluid, to pass through the hydrophobic membrane while preventing fluid within the fluid cassette 110 to pass therethrough. The air may then be vented to atmosphere through the air vent valve 90.

The fluid cassette 110 may also include one or more retention features configured to interact with the console 20 to retain the fluid cassette 110 in the receptacle 52 of the console 20. For example, the fluid cassette 110 may include a retention tab 120 extending from a lower edge of the housing 112 of the fluid cassette 110 and/or a retention tab 124 extending from an upper edge 115 of the housing 112 of the fluid cassette 110, configured to engage mating retention features of the console 20, as described in U.S. Provisional Application Ser. No. 63/597,481, entitled Fluid Management System With Disposable Fluid Cassette, filed on Nov. 9, 2023, the contents of which are hereby incorporated by reference in their entirety.

Figure 5:
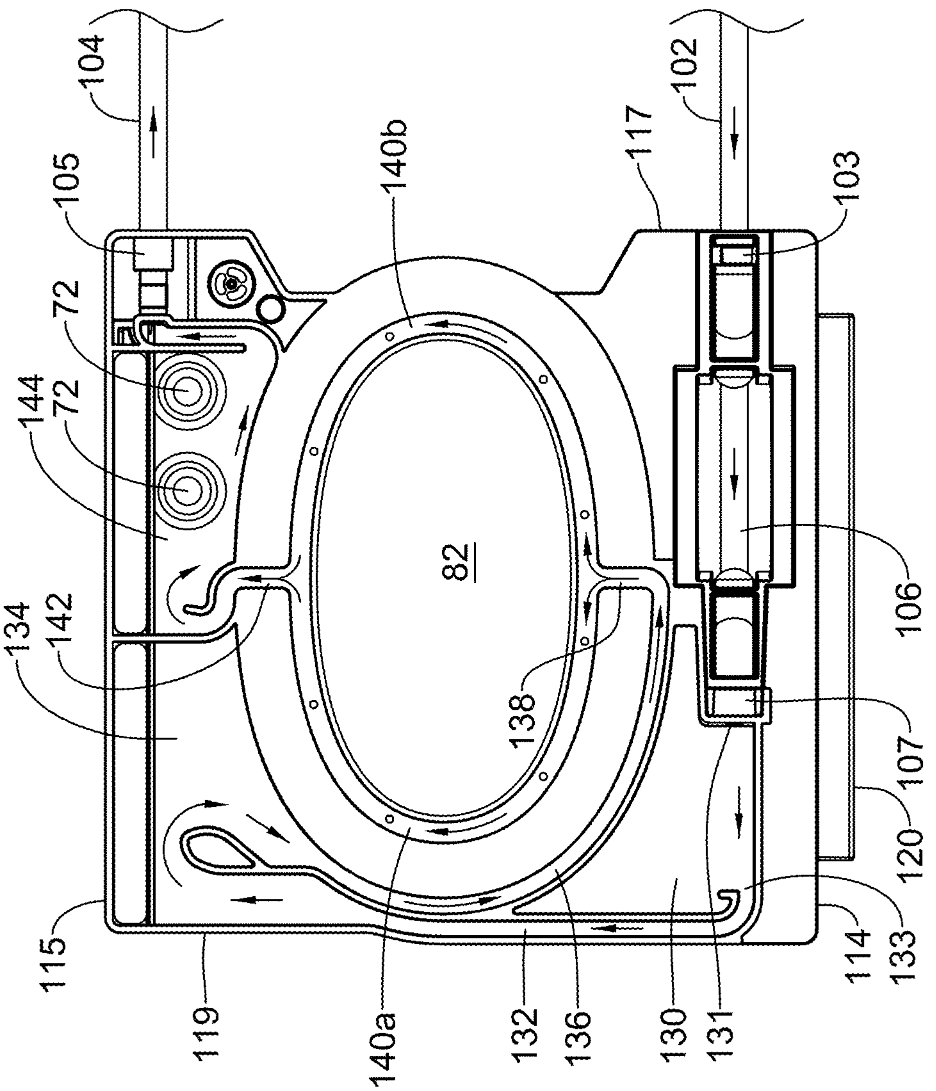
FIG. 5 is a cross-sectional view of the fluid cassette of FIGS. 3 and 4 showing the internal fluid pathway therethrough.

The internal flow pathway through the fluid cassette 110 is shown with arrows in the cross-sectional view of FIG. 5. Fluid flows into the interior of the fluid cassette 110 through the fluid inlet port 103 from the inflow tubing 102, and then passes through the pump tubing 106 as the pump tubing 106 is cyclically compressed by the rollers of the inflow pump 60. The fluid then flows into a fluid damping chamber 130 configured to reduce pressure fluctuations of the pulsatile fluid flow exiting the pump tubing 106 created by the inflow pump 60, and thus smoothen the fluid flow as the fluid exits the fluid damping chamber 130. The fluid damping chamber 130 may include a single fluid inlet 131 and a single fluid outlet 133. The single fluid inlet 131 and the single fluid outlet 133 may be located on opposite sides of the fluid damping chamber 130, such that fluid flows into the fluid damping chamber 130 through the fluid inlet 131 and flows out of the fluid damping chamber 130 through the fluid outlet 133. More details of the fluid damping chamber 130 will be described herein, in regard to FIG. 6.

As fluid exits the fluid damping chamber 130 through the fluid outlet 133 the fluid flows upward through the ascending fluid pathway 132. The ascending fluid pathway 132 interconnects the fluid damping chamber 130 with a first air vent chamber 134. The fluid then exits the first air vent chamber 134 in a downward direction along a descending fluid pathway 136. As shown in FIG. 5, the descending fluid pathway 136 may be an arcuate pathway extending from an upper region above the oval opening 82 to a lower region below the oval opening 82.

The fluid may then enter a bifurcated fluid pathway **140*a*/140*b* from the descending fluid pathway 136 as the fluid passes through a fluid warmer inlet channel 138 interconnecting the descending fluid pathway 136 and the bifurcated fluid pathway 140*a*/140*b*. The bifurcated fluid pathway 140*a*/140*b* includes a first fluid warming pathway 140*a* extending from the fluid warmer inlet channel 138 in a first direction and a second fluid warming pathway 140*b* extending from the fluid warmer inlet channel 138 in a second, generally opposite direction. The first fluid warming pathway 140*a* may extend around a first portion of the oval opening 82 on a first side of the oval opening 82 and the second fluid warming pathway 140*b* may extend around a second portion of the oval opening 82 on a second, opposite side of the oval opening 82. The bifurcated fluid pathway 140*a*/140*b* may then converge at a fluid mixing channel 142 located above the oval opening 82. Thus, the oval opening 82 may be located between the fluid mixing channel 142 and the fluid warmer inlet channel 138, such that the fluid mixing channel 142 is positioned above the oval opening 82 and the fluid warmer inlet channel 138 is positioned below the oval opening 82. Fluid may flow upward from the fluid mixing channel 142 into a second air vent chamber 144. The fluid may then exit the second air vent chamber 144 to the outflow tubing 104 through the outlet port 105**.

Figure 6:
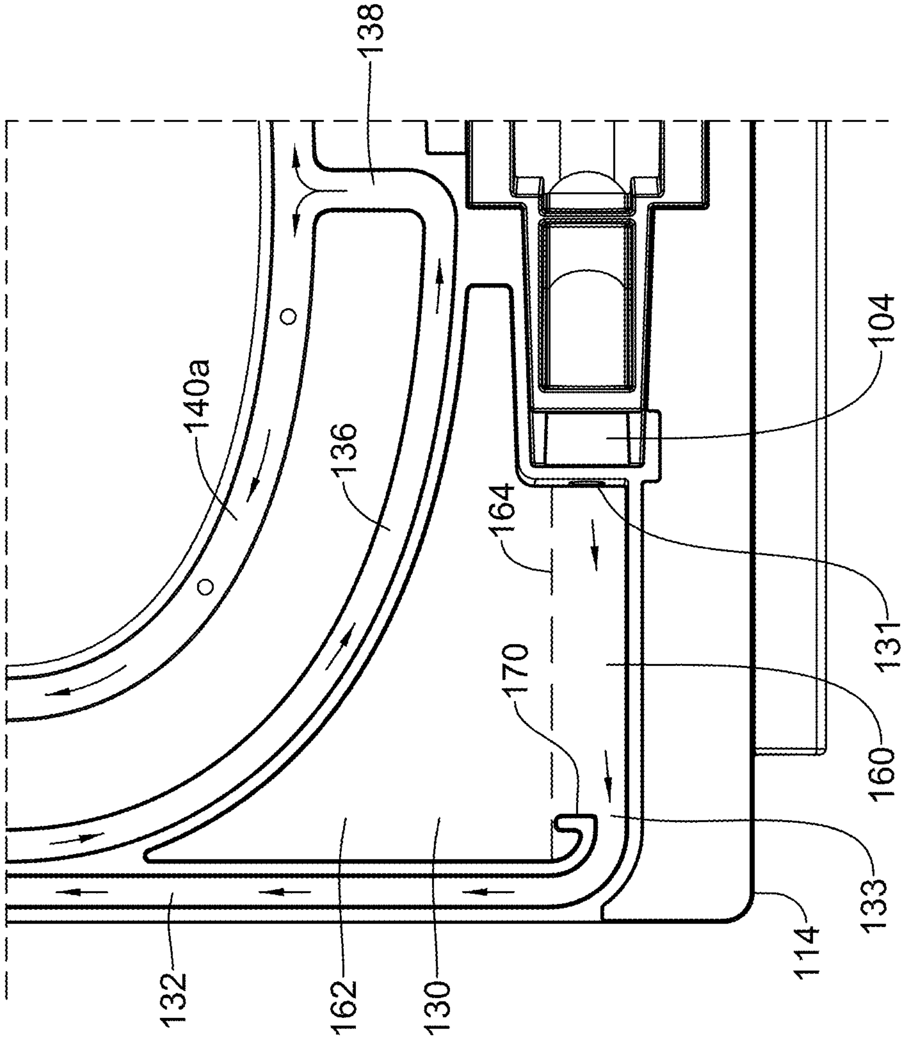
FIG. 6 is an enlarged cross-sectional view of a portion of the fluid cassette of FIG. 5 showing the damping chamber.

FIG. 6 is an enlarged view of the portion of the fluid cassette 110 including the fluid damping chamber 130. During usage of the fluid cassette 110, a volume of fluid 160 may fill the lower portion of the fluid damping chamber 130 while a volume of air 162 is trapped in the upper portion of the fluid damping chamber 130. The fluid level 164 is the direct interface between the volume of fluid 160 and the volume of air 162. The fluid damping chamber 130 may be designed to substantially smoothen the pulsatile fluid flow from the inflow pump 60 for fluid flows up to 800 ml/min, in some instances. For example, it has been found that sizing the fluid damping chamber 130 such that the volume of air 162 is at least 38 ml substantially smoothens the pulsatile fluid prior to exiting the fluid damping chamber 130. Accordingly, the fluid damping chamber 130 may be sized to provide a volume of air 162 of 38 ml or more, or 40 ml or more, in some instances. For instance, the fluid damping chamber may be sized to provide a volume of air 162 of about 38 ml to 42 ml, during use.

Furthermore, as noted above, the fluid damping chamber 130 may include a single fluid inlet 131 and a single fluid outlet 133 located on opposite sides of the fluid damping chamber 130, such that fluid flows into the fluid damping chamber 130 through the fluid inlet 131 and flows out of the fluid damping chamber 130 through the fluid outlet 133. The fluid inlet 131 and the fluid outlet 133 may be positioned near a base of the fluid damping chamber 130. The fluid damping chamber 130 may be configured such that the upper extent of the fluid outlet 133 is lower (i.e., closer to the lower edge 114 of the fluid cassette 110) than the upper extent of the fluid inlet 131. This ensures that the fluid level 164 is above the upper extent of the fluid outlet 133 such that air from the volume of air 162 is not pulled out of the fluid damping chamber 130 into fluid exiting the fluid damping chamber 130 though the fluid outlet 133 into the ascending fluid pathway 132, which could otherwise occur at high flowrates. In some instances, the fluid outlet 133 may include a lip 170 extending upward from the upper extent of the opening of the fluid outlet 133 into the fluid damping chamber 130. The lip 170 may have any desired height. In some instances, the height of the lip 170 may be sized such that the fluid level 164 is above the upper extent of the lip 170. In other instances, the fluid level 164 may impinge the lip 170.

Prior to any interaction between the fluid management system 10, the attached endoscope, and the patient, the fluid cassette 110 and outflow tubing 104 may be primed. Priming refers to filling the fluid cassette 110 and outflow tubing 104 with fluid to remove air before a procedure begins. Priming may be necessary because air bubbles that may be introduced during a procedure can impair visibility. In some cases, it may be desirable to complete the priming procedure in more than one stage when setting up the fluid management system 10 prior to a procedure. For example, it is contemplated that one person can prime the fluid cassette 110 while another person sets up the outflow tubing 104 with the endoscope. However, the fluid management system 10 may need to be able to maintain the fluid cassette 110 in a primed configuration while the outflow tubing 104 is being set up and the physician is preparing for the procedure. Then, once the endoscope is connected and everything is ready, a second priming stage can be started to push the air out of the outflow tubing 104 and the endoscope if so desired. In some cases, the second stage of the priming procedure may be omitted. However, performing the second stage of the priming procedure may reduce the amount of time required to begin a procedure when the physician is ready. It is contemplated that performing the priming procedure incrementally or in more than one stage may allow for flexibility when setting up the fluid management system 10 before a procedure and/or may reduce down time for the physician prior to starting a procedure.

Figure 7:
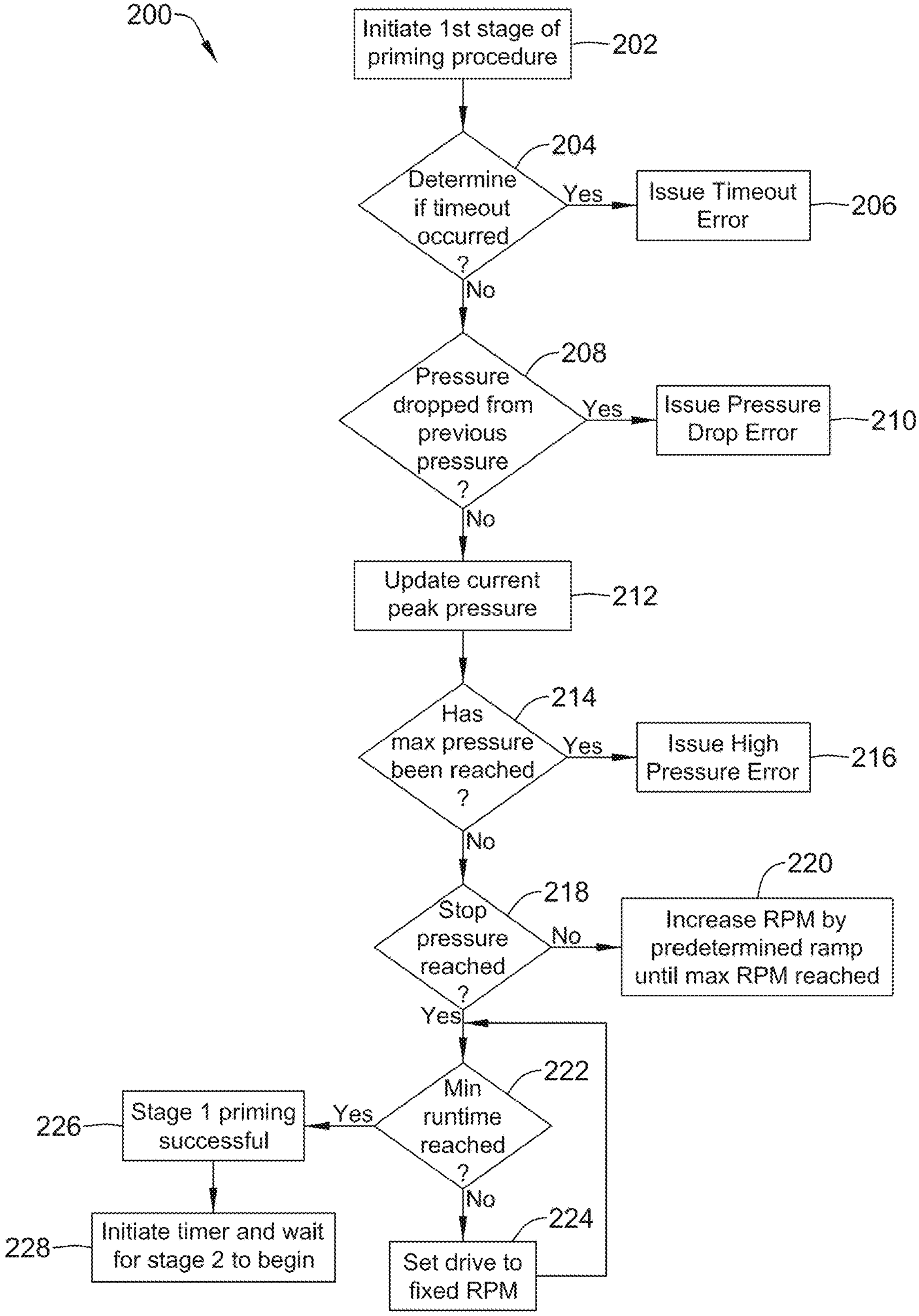
FIG. 7 is an illustrative flow chart of a method for performing a first stage of a priming procedure.

The fluid management system 10 may be configured to include a two-stage priming procedure. In some cases, the first stage of the priming procedure may occur or be performed up to one hour before the second stage of the priming procedure. This is just one example. In other cases, the time delay between the completion of the first stage and the initialization of the second stage may be less than one hour or greater than one hour. FIG. 7 is an illustrative flow chart 200 of a first stage of an illustrative method for priming the fluid management system 10 and/or the endoscope. Generally, the first stage of the priming procedure may purge air from the fluid cassette 110. During the first stage of the priming procedure, the inflow pump 60 pulls fluid from the source into the fluid cassette 110 via the inflow tubing 102 and the pump tubing 106, pushing the air out of the fluid path through the air vent valve 90 or other air vents located at or near the top of the fluid cassette 110. Once the air is removed from the fluid path, the pressure within the flow path of the fluid cassette quickly increases. The first stage of the priming procedure may be successfully completed and stops the pump when the pump pressure reaches 360 mmHg.

Prior to performing the first stage of the priming procedure, the user may perform a set-up procedure. The user may use the touch screen interface 42 to enter the set-up procedure. It is contemplated that the user may select between a step-by-step guide which includes a plurality of screens which guides the user through each step of the set-up procedure or a quick setup guide which provides a consolidated view of the steps in the set-up procedure. For example, prior to priming the fluid cassette 110, the inflow tubing 102 may be fluidly coupled with one or more fluid sources and clamps that are positioned along the inflow tubing 102 may be opened to allow fluid flow through the inflow tubing 102. Further, the user should install the fluid cassette 110 within the receptacle 52 and close the door 50. Additionally, the user may verify that a clamp 150 (see, for example, FIG. 8) secured to the outflow tubing 104 is closed to prevent a flow of fluid through the outflow tubing 104. The clamp 150 may be movable between a closed configuration configured to block a flow of fluid through the outflow tubing 104 and an open configuration configured to allow a flow of fluid through the outflow tubing 104. The closed clamp 150 may allow fluid to accumulate within the fluid cassette 110 and allow the pressure to increase.

In some embodiments, the fluid management system 10 may be configured to perform pressure sensor checks and zeroing prior to performing the first stage of the priming procedure. As described above, the fluid management system may contain two pump pressure sensors 70. The two pump pressure sensors 70 may be used to check one another. For example, once the fluid cassette 110 is inserted into the console and the door 50 is closed, the cross-checking may begin. During the pressure sensor checks, a pressure sensor that is out of range (e.g., ±30 mmHg) for 500 milliseconds may considered a critical failure. An alert or error message may be displayed to the user via the touch screen interface 42. The error message may be an alphanumeric message, an audio alert, another type of visual alert, or the like. In some embodiments, the pressure sensor startup cross check may use the priming pressure at the start of priming and then the high pressure as the only pressure sensor cross check. Said differently, the pressure sensor cross check may occur during the priming procedure and utilize pressure measurements from the priming procedure as the cross check.

Zeroing the pressure sensors 70 may also be performed before or at the start of the priming procedure. If the zeroing one or more of the pressure sensors fails (e.g., the offset needed to set the pressure sensor(s) to zero is greater than a predetermined threshold), then the priming procedure may not be performed. In some cases, the door closure dynamics may have an impact on the time to zero, zeroing may be performed prior the start of the priming. This may allow sufficient time for the debounce generated by the door 50 closing to settle down before zeroing. Zeroing may be required before the fluid management system 10 uses the pressure sensors to control the priming procedure and/or to control a procedure. In some embodiments, it may be desirable to zero the pressure sensors after the first and/or second stage of the priming procedure has been completed. However, performing the zeroing procedure with fluid in the fluid flow path of the fluid cassette 110 may require characterization of the system and/or tight tolerances in the console 20, fluid cassette 110, and/or the priming procedure.

To begin the priming procedure, the user may initiate or start a first stage of the priming procedure at the touch screen interface 42, as shown at block 202. The first stage may be initialized at the touch screen interface 42 through actuation of a touchscreen interface, actuating a button, or the like. The controller 30 may be configured to execute the steps of the priming procedure. When the first stage of the priming is initiated, the controller 30 may start a timer. The controller 30 may continually compare a cycle time or a length of time that has elapsed since initiation of the first stage of the priming procedure with a predetermined maximum cycle length to determine if a timeout has occurred, as shown at block 204. For example, the first stage of the priming procedure must be completed within a predetermined length of time. If the first stage of the priming procedure takes too much time or exceeds the predetermined length of time, a timeout error may be issued and the first stage of the priming procedure stopped, as shown at block 206. The timeout error may occur at any point during the first stage of the priming procedure if the time elapsed exceeds the predetermined maximum allowable completion time. The timeout error may be an alphanumeric message displayed on the touch screen interface 42, an audio alert, other visual alert, or the like. If the elapsed time has not exceeded a predetermined maximum length of time, the first stage of the priming procedure may continue.

Further, the controller 30 may be configured to continually monitor the pump pressure and/or the pressure within the flow path of the fluid cassette 110. The controller 30 may compare a current pressure to a previous pressure to determine if the pressure has dropped, as shown at block 208. For example, the controller 30 may be configured to obtain pressure measurements at predetermined time intervals. The controller 30 may compare a most recently acquired pressure measurement with the pressure measurement immediately preceding the current pressure measurement. If the current pressure measurement is less than the preceding pressure measurement, a pressure drop error may be issued and the first stage of the priming procedure stopped, as shown at block 210. A pressure drop that occurs within the flow path of the fluid cassette 110 may be indicative of a fluid leak in the flow path. Pressure drop errors may be generated at any time during the priming procedure if the pressure decreases by a predetermined amount or at any pressure decrease. The pressure drop error may be an alphanumeric message displayed on the touch screen interface 42, an audio alert, other visual alert, or the like. If the pressure does not lower or drop, the first stage of the priming procedure may continue.

When the first stage of the priming procedure is initiated, the controller 30 may be configured to activate the inflow pump 60 and increase the revolutions per minute (RPM) thereof until a maximum RPM is obtained to start a flow of fluid through the system and raise the pressure within the flow path of the fluid cassette 110. It is contemplated that the controller 30 may control the RPM (e.g., increase and/or decrease the RPM) of the inflow pump 60 to obtain a predetermined pressure. The controller 30 may continually monitor and store a current peak pressure measurement, as shown at block 212. In some cases, the pressure measurement may be updated at predetermined time intervals. The controller 30 may be configured to compare the current pressure measurement with a predetermined maximum pressure to determine if the maximum pressure has been met or exceeded, as shown at block 214. In some embodiments, the maximum pressure may be about 600 mmHg. This is just an example. The maximum pressure may be less than or greater than 600 mmHg, as desired. If the pump pressure meets or exceeds the predetermined maximum pressure, the controller 30 may issue a high-pressure error, as shown at block 216. High-pressure errors may occur at any time during the first stage of the priming procedure when the measured pressure meets or exceeds the predetermined maximum pressure. The high-pressure error may be an alphanumeric message displayed on the touch screen interface 42, an audio alert, other visual alert, or the like. A high-pressure may be indicative of a block or obstruction in the flow path of the fluid cassette 110. If the pressure does not exceed a predetermined maximum pressure, the first stage of the priming procedure may continue.

As the controller 30 is increasing or ramping the RPM of the inflow pump 60, the controller 30 may be configured to compare the current peak pressure to a predetermined stop pressure to determine if the stop pressure has been reached, as shown at block 218. In some cases, the stop pressure may about 360 mmHg. This is just an example. The stop pressure may be less than or greater than 360 mmHg, as desired. If the stop pressure has not been reached, the controller 30 may continue to increase the RPM of the inflow pump 60 until the maximum RPM is reached, as shown at block 220. The maximum RPM or speed may be maintained until the stop pressure is reached. If the stop pressure is not reached, an alert may be displayed on the touch screen interface 42. The "pressure not achieved" error may be an alphanumeric message displayed on the touch screen interface 42, an audio alert, other visual alert, or the like.

If the stop pressure has been reached, the controller 30 may compare a current runtime (e.g., a length of time the first stage of the priming procedure has been in process) to a predetermined minimum runtime to determine if the minimum runtime has been reached, as shown at block 222. If the minimum runtime has not been reached, the controller 30 may set the inflow pump 60 to a fixed RPM, as shown at block 224, and allow the inflow pump 60 to run until the minimum runtime has been reached. When the minimum runtime has been reached, a successful first stage of the priming procedure has been completed and the inflow pump 60 stopped, as shown at block 226. An indication that the first stage of priming has been successfully completed may also be displayed on the display 44. Upon successful completion of the first stage of priming, the controller 30 may initiate a timer and wait for the second stage of the priming procedure to begin, as shown at block 228.

It is contemplated that the timer may be countdown timer which begins at a maximum allowable time between the first stage of the priming procedure and the second stage of the priming procedure. For example, in some cases, the fluid management system 10 can wait up to 60 minutes between the completion of the first stage of the priming procedure and the start of the second stage of the priming procedure. In some cases the maximum allowable time allowed between the successful completion of the first stage of priming and the initiation of the second stage of priming may be between 30 minutes and 90 minutes, between 45 minutes and 75 minutes, between 50 minutes and 70 minutes, about 60 minutes, or other desired amount of time. Prior to initiating the second stage of the priming procedure, the controller 30 may be configured to determine if the timer has expired or the maximum allowable time between stages has been surpassed. In one example, if sixty minutes or more elapses between the completion of the first stage of the priming procedure and the start of the second stage of the priming procedure, the controller 30 may be configured to display a timeout error and the first stage of the priming procedure may have to be recompleted or performed again. In some embodiments, the maximum allowable time between the first stage of the priming procedure and the second stage of the priming procedure may be less than sixty minutes or more than sixty minutes, as desired. It is further contemplated that the timer may count up and compare the elapsed time to the maximum allowable time between the first stage of the priming procedure and the second stage of the priming procedure.

Figure 8:
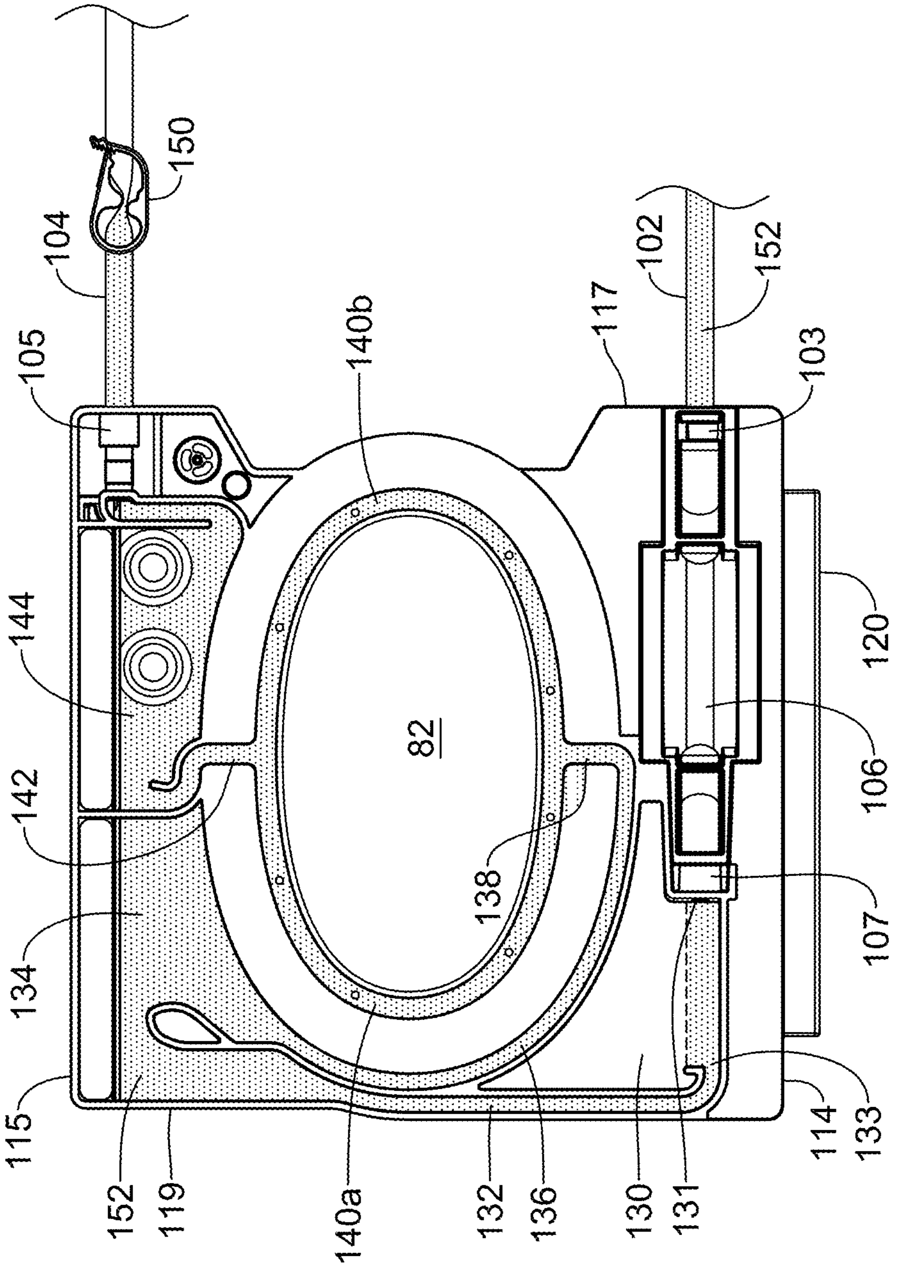
FIG. 8 is a cross-sectional view of a portion of the fluid cassette of FIGS. 3 and 4 showing the internal fluid pathway after the first stage of a priming procedure.
Figure 9:
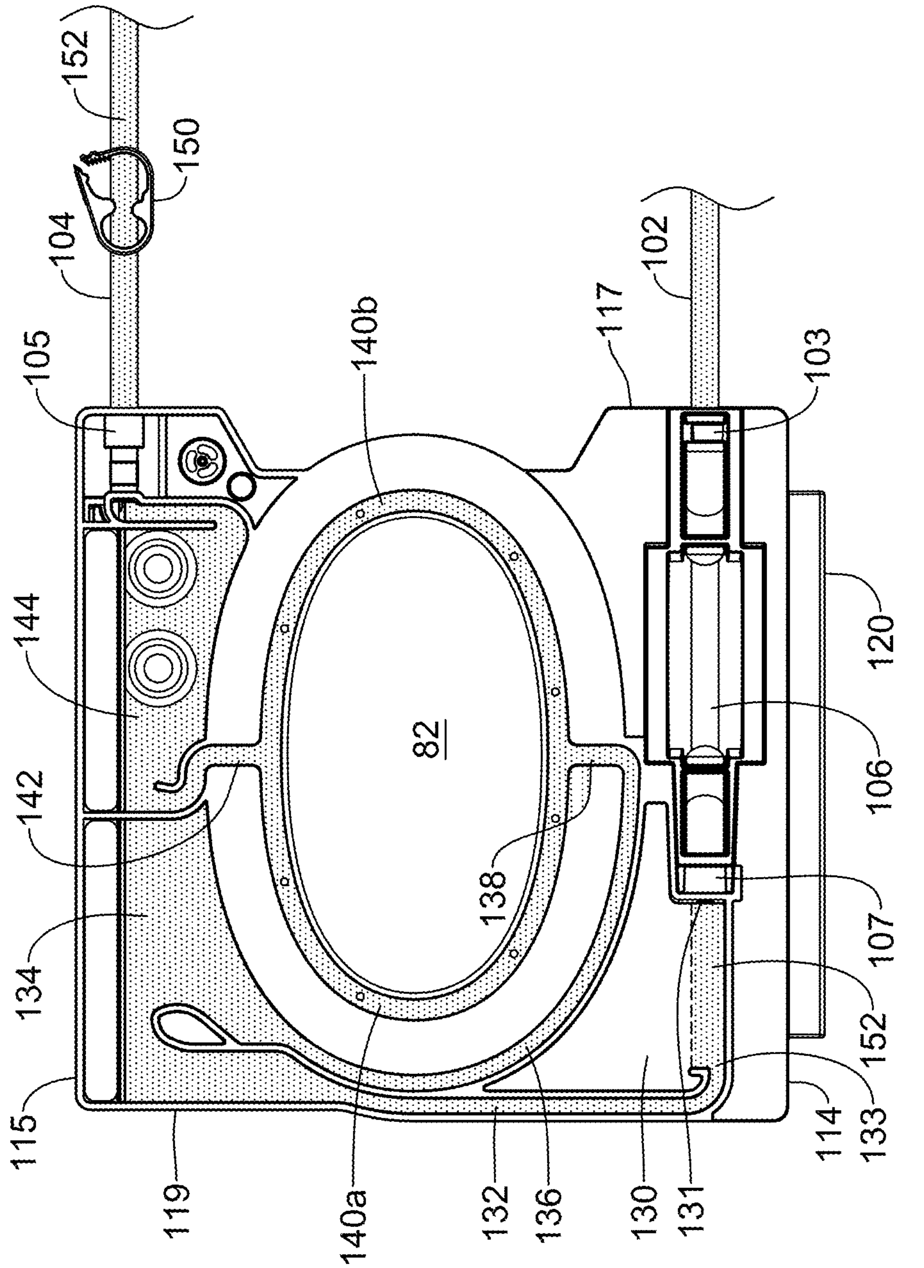
FIG. 9 is a cross-sectional view of a portion of the fluid cassette of FIGS. 3 and 4 showing the internal fluid pathway at the beginning of a second stage of a priming procedure.

When the first stage of the priming procedure is complete, the flow path of the fluid cassette 110 may be filled with fluid 152, as is schematically shown in FIG. 8 which illustrates a schematic cross-sectional view of the fluid cassette 110 after the first stage of the priming procedure. The clamp 150 on the outflow tubing 104 is closed which maintains the pressure within the fluid cassette 110 at a substantially constant pressure. Releasing or opening the clamp 150 on the outflow tubing 104 as is schematically shown in FIG. 9, which illustrates a schematic cross-sectional view of the fluid cassette 110 with the clamp in the open configuration, will allow fluid 152 to flow through the outflow tubing 104 and into the endoscope (if connected) causing a notable drop in the pressure in the fluid cassette 110. This pressure drop may initiate or start the second stage of the priming procedure. In other words, when the system senses the pressure drop within the fluid cassette 110 at the pressure sensors 70, the controller may automatically initiate or start the second stage of the priming procedure. Thus, opening the clamp on the outflow tubing 104 of the fluid tubing set 100 may automatically initiate or start the second stage of the priming procedure.

Figure 10:
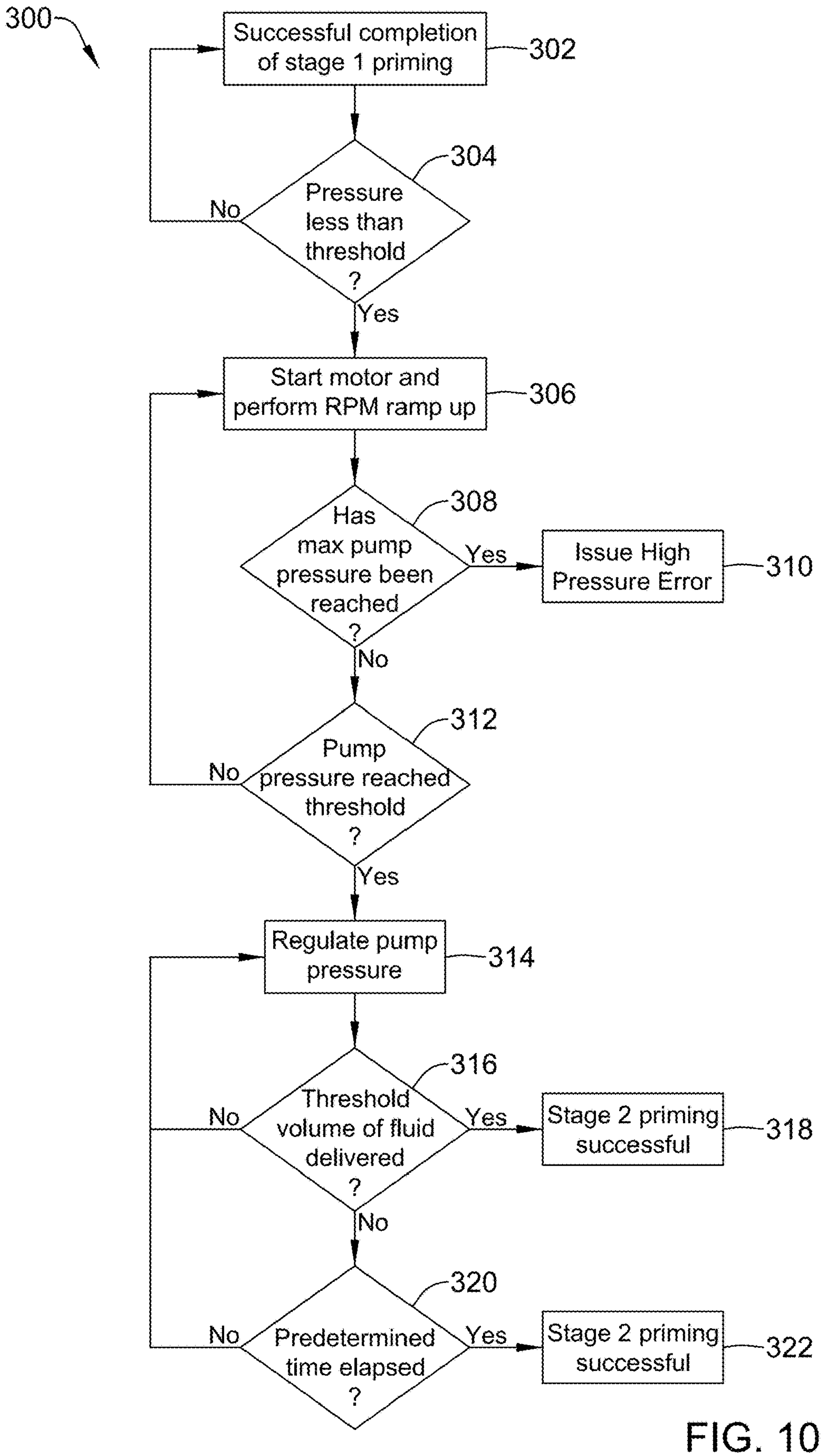
FIG. 10 is an illustrative flow chart of a method for performing a second stage of a priming procedure.

FIG. 10 is an illustrative flow chart 300 of a second stage of an illustrative method for priming the fluid management system 10 and/or the endoscope. Generally, the second stage of the priming procedure may purge air from the outflow tubing 104 and endoscope (if connected). To begin the second stage of the priming procedure the first stage of the priming procedure must first be successfully completed, as shown at block 302. After successful completion of the first stage of the priming procedure, the controller 30 may monitor the pump pressure of the inflow pump 60 to determine if the pressure has dropped or decreased from the pressure at the completion of the first stage of the priming procedure, as shown at block 304. If the pressure has not dropped, the controller 30 may continue to monitor the pressure of the inflow pump 60 to identify a pressure drop. When the pressure decreases below a predetermined threshold pressure, the controller 30 may determine that the clamp 150 has been removed and the second stage of the priming procedure should be initiated.

To initiate the second stage of the priming procedure, the motor of the inflow pump 60 may be activated and the RPMs of the inflow pump 60 increased or ramped up, as shown at block 306. The controller 30 may be configured to compare the current pressure measurement with a predetermined maximum pressure to determine if the maximum pressure has been met or exceeded, as shown at block 308. In some embodiments, the maximum pressure may be about 600 mmHg. This is just an example. The maximum pressure may be less than or greater than 600 mmHg, as desired. If the pump pressure meets or exceeds the predetermined maximum pressure, the controller 30 may issue a high-pressure error, as shown at block 310. A high-pressure error may occur at any time during the second stage of the priming procedure if the measured pressure exceeds the maximum pressure. The high-pressure error may be an alphanumeric message displayed on the touch screen interface 42, an audio alert, other visual alert, or the like. A high-pressure may be indicative of a block or obstruction in the flow path of the fluid cassette 110 or a fluid channel of the endoscope. If the pressure does not exceed a predetermined maximum, the second stage of the priming procedure may continue.

As the controller 30 is increasing or ramping the RPM of the inflow pump 60, the controller 30 may be configured to compare the current peak pressure to a predetermined threshold pressure to determine if the threshold pressure has been reached, as shown at block 312. In some cases, the threshold pressure may about 540 mmHg. This is just an example. The threshold pressure may be less than or greater than 540 mmHg, as desired. If the threshold pressure has not been reached, the controller 30 may continue to increase the RPM of the inflow pump 60, as shown at block 306.

Once the pump pressure threshold has been reached, the controller 30 may increase and/or decrease the motor speed to maintain the pressure at the threshold pressure, as shown at block 314. The fluid inflow pump 60 may be maintained at the threshold pressure until at least one of two conditions is met. For example, the controller 30 may determine if a minimum or threshold volume of fluid has been delivered through the system, as shown at block 316. If the minimum or threshold volume of fluid has been delivered through the system, the second stage of the priming procedure may be considered successful and complete, as shown at block 318. The flow volume may be determined or measured using the rotations of the fluid inflow pump 60. If the minimum or threshold volume of fluid has not been delivered through the system, the fluid inflow pump 60 may continue to be maintained at the threshold pressure and the controller 30 may determine if a predetermined length of time has elapsed from the initiation of the second stage of the priming procedure, as shown at block 320. If the minimum predetermined length of time has elapsed, the second stage of the priming procedure may be considered successful and complete, as shown at block 322. If the minimum predetermined length of time has not been met or exceeded, the fluid inflow pump 60 may continue to be maintained at the threshold pressure until either the threshold volume of fluid has been delivered or the predetermined length of time has elapsed. It is contemplated that in some embodiments, the controller 30 may check the elapsed time prior to or substantially simultaneously with checking the volume of fluid delivered. In some cases, the controller 30 may be configured to select between the successful completion criteria (e.g., fluid volume or elapsed time) based on a size of the endoscope. For example, the controller 30 may rely on only one of the minimum fluid volume or minimum time elapsed to determine if the second stage of the priming procedure has been successfully completed.

It is contemplated that either the first stage or the second stage of the priming procedure may be cancelled at any time by the user via the touch screen interface 42. However, if the first stage of the priming procedure is not successfully completed, the fluid management system 10 may be prevented from entering a procedure mode. If the first stage of the priming procedure is cancelled, the user may be instructed to perform the first stage of the priming procedure before being able to perform the second stage of the priming procedure or before entering a procedure mode. In one example, an alphanumeric message may be displayed on the touch screen interface 42. The fluid management system 10 may be allowed to enter a procedure mode if the second stage of the priming procedure is cancelled. For example, the fluid management system 10 may enter a procedure mode upon the successful completion of the second stage of the priming procedure or upon cancellation of the second stage of the priming procedure. As described above, if the second stage of the priming procedure is not initialized within the predetermined length of time (e.g., 60 minutes), the user may be instructed to perform the first stage of the priming procedure again.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The scope of the disclosure is, of course, defined in the language in which the appended claims are expressed.

What is claimed is:

1. A fluid management system, the system comprising:
a fluid management console, comprising:
a housing;
a controller housed within the housing;
an inflow pump disposed within the housing; and
a user input interface;
a fluid cassette configured to be received within a receptacle of the housing of the fluid management console, the fluid cassette comprising:
a housing defining a fluid pathway therethrough;

an inflow tubing extending from the housing; and
an outflow tubing extending from the housing; and
a clamp secured to the outflow tubing, the clamp movable between a closed configuration configured to block a flow of fluid through the outflow tubing and an open configuration configured to allow a flow of fluid through the outflow tubing;
wherein the controller of the fluid management console is configured to perform a first stage of a priming procedure in response to a user input at the user input interface and a second stage of the priming procedure in response to a pressure drop within the fluid pathway of the fluid cassette;
wherein the clamp is in the closed configuration during the first stage of the priming procedure and the open configuration during the second stage of the priming procedure.

2. The fluid management system of claim 1, further comprising one or more pressure sensors disposed within fluid management console, the one or more pressure sensors configured to monitor a pressure within the fluid pathway of the fluid cassette.

3. The fluid management system of claim 1, wherein during the first stage of the priming procedure, the controller is configured to activate the inflow pump.

4. The fluid management system of claim 1, wherein during the first stage of the priming procedure, the controller is configured to monitor a pressure within the fluid pathway of the fluid cassette.

5. The fluid management system of claim 4, wherein if the pressure within the fluid pathway exceeds a predetermined maximum pressure, the controller is configured to issue a high-pressure error.

6. The fluid management system of claim 4, wherein if the pressure the fluid pathway drops, the controller is configured to issue a pressure drop error.

7. The fluid management system of claim 1, wherein the controller is configured to increase a revolutions per minute of the inflow pump until a predetermined maximum speed is achieved.

8. The fluid management system of claim 1, wherein during the second stage of the priming procedure a revolutions per minute of the inflow pump is increased until a threshold pressure within the fluid pathway of the fluid cassette is reached.

9. The fluid management system of claim 1, wherein the second stage of the priming procedure is successfully completed with a minimum fluid volume has been delivered through the fluid pathway of the fluid cassette or a minimum cycle time has elapsed.

10. A fluid management system, the system comprising:
a fluid management console, comprising:
a housing;
a controller housed within the housing;
an inflow pump disposed within the housing; and
a user input interface; and
a fluid cassette configured to be received within a receptacle of the housing of the fluid management console, the fluid cassette comprising:
a housing defining a fluid pathway therethrough;
an inflow tubing extending from the housing; and
an outflow tubing extending from the housing;
wherein the controller of the fluid management console is configured to perform a first stage of a priming procedure in response to a user input at the user input interface and a second stage of the priming procedure in response to a pressure drop within the fluid pathway of the fluid cassette;
wherein if the second stage of the priming procedure is not initiated within a predetermined length of time after completion of the first stage of the priming procedure, the controller is configured to instruct the user to repeat the first stage of the priming procedure.

11. The fluid management system of claim 10, wherein the predetermined length of time is one hour.

12. A fluid management system, the system comprising:
a fluid management console, comprising:
a housing;
a controller housed within the housing;
an inflow pump disposed within the housing; and
a user input interface; and
a fluid cassette configured to be received within a receptacle of the housing of the fluid management console, the fluid cassette comprising:
a housing defining a fluid pathway therethrough;
an inflow tubing extending from the housing; and
an outflow tubing extending from the housing;
wherein the controller of the fluid management console is configured to perform a first stage of a priming procedure in response to a user input at the user input interface and a second stage of the priming procedure in response to a pressure drop within the fluid pathway of the fluid cassette;
wherein if a cycle time of the first stage of the priming procedure exceeds a predetermined maximum cycle time, the controller is configured to issue a timeout error.

13. A fluid management system, the system comprising:
a fluid management console, comprising:
a housing;
a controller housed within the housing;
an inflow pump disposed within the housing; and
a user input interface; and
a fluid cassette configured to be received within a receptacle of the housing of the fluid management console, the fluid cassette comprising:
a housing defining a fluid pathway therethrough;
an inflow tubing extending from the housing; and
an outflow tubing extending from the housing;
wherein the controller of the fluid management console is configured to perform a first stage of a priming procedure in response to a user input at the user input interface and a second stage of the priming procedure in response to a pressure drop within the fluid pathway of the fluid cassette;
wherein upon reaching a predetermined stop pressure and a minimum runtime, the first stage of the priming procedure is successfully completed.

14. A fluid management system, the system comprising:
a fluid management console, comprising:
a housing;
a controller housed within the housing;
an inflow pump disposed within the housing; and
a user input interface; and
a fluid cassette configured to be received within a receptacle of the housing of the fluid management console, the fluid cassette comprising:
a housing defining a fluid pathway therethrough;
an inflow tubing extending from the housing; and
an outflow tubing extending from the housing; and
a clamp secured to the outflow tubing, the clamp movable between a closed configuration configured to block a flow of fluid through the outflow tubing and an open configuration configured to allow a flow of fluid through the outflow tubing;

wherein the controller of the fluid management console is configured to perform a first stage of a priming procedure in response to a user input at the user input interface and a second stage of the priming procedure in response to a pressure drop within the fluid pathway of the fluid cassette;

wherein opening the clamp initiates the second stage of the priming procedure.

15. The fluid management system of claim 14, wherein the first stage of the priming procedure is configured to remove air from the inflow tubing, the fluid pathway of the fluid cassette, and the outflow tubing to a location of the clamp.

16. The fluid management system of claim 14, wherein the second stage of the priming procedure is configured to remove air from an entirety of the outflow tubing and a connected device.

17. The fluid management system of claim 15, wherein the second stage of the priming procedure is configured to remove air from an entirety of the outflow tubing and a connected device.

18. A fluid management system, the system comprising:

a fluid management console, comprising:

a housing;

a controller housed within the housing;

an inflow pump disposed within the housing; and a user input interface; and a fluid cassette configured to be received within a receptacle of the housing of the fluid management console, the fluid cassette comprising:

a housing defining a fluid pathway therethrough;

an inflow tubing extending from the housing; and an outflow tubing extending from the housing;

wherein the controller of the fluid management console is configured to perform a first stage of a priming procedure in response to a user input at the user input interface and a second stage of the priming procedure in response to a pressure drop within the fluid pathway of the fluid cassette, the second stage of the priming procedure configured to begin after a successful completion of the first stage of the priming procedure;

wherein upon reaching a predetermined stop pressure and a minimum runtime, the first stage of the priming procedure is successfully completed.

19. The fluid management system of claim 18, wherein if the second stage of the priming procedure is not initiated within a predetermined length of time after completion of the first stage of the priming procedure, the controller is configured to instruct the user to repeat the first stage of the priming procedure.

* * * * *